US007195893B2

(12) United States Patent
Parker et al.

(10) Patent No.: US 7,195,893 B2
(45) Date of Patent: Mar. 27, 2007

(54) NUCLEIC ACIDS ENCODING $\alpha_2\delta$ CALCIUM CHANNEL SUBUNITS AND METHODS FOR MAKING AND USING THEM

(75) Inventors: David Parker, Maple Ridge (CA); Xianghong Xu, Vancouver (CA); Afsheen Khawaja, Surrey (CA); Janette Mezeyova, Vancouver (CA); Terrance P. Snutch, Vancouver (CA)

(73) Assignee: Neuromed Pharmaceuticals Ltd., Vancouver (CA)

( * ) Notice: Subject to any disclaimer, the term of this patent is extended or adjusted under 35 U.S.C. 154(b) by 0 days.

(21) Appl. No.: 10/918,602

(22) Filed: Aug. 12, 2004

(65) Prior Publication Data
US 2005/0089961 A1  Apr. 28, 2005

Related U.S. Application Data

(60) Provisional application No. 60/495,634, filed on Aug. 14, 2003.

(51) Int. Cl.
*C12P 21/06* (2006.01)
(52) U.S. Cl. .................................... 435/69.1
(58) Field of Classification Search ............... 530/350; 435/69.1; 514/12
See application file for complete search history.

(56) References Cited

U.S. PATENT DOCUMENTS

| 5,386,025 | A   | 1/1995  | Jay et al. ............... 536/23.5 |
| 6,309,858 | B1  | 10/2001 | Dietrich et al. ........... 435/69.1 |
| 6,358,706 | B1  | 3/2002  | Dubin et al. ............. 435/69.1 |
| 6,441,156 | B1* | 8/2002  | Lerman et al. ........... 536/23.5 |

FOREIGN PATENT DOCUMENTS

| WO | WO 95/04144  | 2/1995 |
| WO | WO-95/04822  | 2/1996 |
| WO | WO 98/38301  | 9/1998 |
| WO | WO 01/02561  | 1/2001 |
| WO | WO-01/19870  | 3/2001 |
| WO | WO-01/20336  | 3/2001 |

OTHER PUBLICATIONS

Brown et al., Cloning and Deletion Mutagenesis of the alpha2sigma Calcium Channel Subunit from Porcine Cerebral Cortex, J. Biol. Chem. 273 (39), p. 25458-25465 (1998).*
GenCore 5.1.6. Result 1 (Reference to J. Biol. Chem. 1998).*
Boardman et al., GENBANK database entry (2004) Accession No. Bx935173.
Hubbard, GENBANK database entry (2002) Accession No. BU133223.
International Search Report for PCT/CA2004/001511, mailed on Jan. 14, 2005, 4 pages.
Angelotti et al., FEBS Lett. (1996) 397:331-337.
Bourinet et al., EMBO J. (1994) 13:5032-5039.
Bourinet et al., Nature Neuroscience (1999) 2:407-415.
Bourinet et al., Proc. Nat'l. Acad. Sci. USA (1996) 93:1486-1491.
Brust et al., Neuropharmacology (1993) 32(11):1089-1102.
Burgess et al., Cell (1997) 88:385-392.
Castellano et al., J. Biol. Chem. (1993) 268:3450-3455.
Castellano et al., J. Biol. Chem. (1993) 268:12359-12366.
Dubel et al., Proc. Nat'l. Acad. Sci. USA (1992) 89:5058-5062.
Dunlap et al., Trends Neurosci. (1995) 18:89-98.
Felix et al., J. Neuroscience (1997) 17(18):6884-6891.
Fletcher et al., Cell (1996) 87:607-617.
Fujita et al., Neuron (1993) 10:585-598.
Gao et al., J. Biol. Chem. (2000) 275(16):12237-12242.
Hobom et al., Eur. J. Neurosci. (2000) 12(4):1217-1226.
Klugbauer et al., J. Neuroscience (1999) 19(2):684-691.
Marais et al., Molec. Pharmacol. (2001) 59(5):1243-1248.
McCleskey et al., Curr. Topics Membr. (1991) 39:295-326.
Mikami et al., Nature (1989) 340:230-233.
Mori et al., Nature (1991) 350:398-402.
Ophoff et al., Cell (1996) 87:543-552.
Perez-Reyes et al., J. Biol. Chem. (1992) 267:1792-1797.
Pragnell et al., FEBS Lett. (1991) 291:253-258.
Qin et al., Mol. Pharmacol. (2002) 62(3):485-496.
Sather et al., Neuron (1993) 11:291-303.
Snutch et al., Neuron (1991) 7:45-57.
Soong et al., Science (1993) 260:1133-1136.
Stea et al., Neuron (1995) 15:929-940.
Stea et al., Proc. Nat'l. Acad. Sci. USA (1994) 91:10576-10580.
Tomlinson et al., Neuropharmacology (1993) 32:1117-1126.
Williams et al., Neuron (1992) 8:71-84.
Williams et al., Science (1992) 257:389-395.
Zhuchenko et al., Nature Genetics (1997) 15:62-69.
Chin, On the Preparation and Utilization of Isolated and Purified Oligonucleotides, unpublished document submitted to the public collection of the Kathrine R. Everett Law Library of the University of North Carolina on Mar. 14, 2002.
Supplementary European Search Report for EP 04761675.0, mailed on Sep. 6, 2006, 3 pages.

* cited by examiner

*Primary Examiner*—Karen Cochrane Carlson
*Assistant Examiner*—Agnes B. Rooke
(74) *Attorney, Agent, or Firm*—Morrison & Foerster LLP

(57) ABSTRACT

A new class of $\alpha_2\delta$ subunits which function in calcium ion channels is described. This class is avian derived.

19 Claims, 6 Drawing Sheets

NUCLEIC ACIDS ENCODING α₂δ CALCIUM CHANNEL SUBUNITS AND METHODS FOR MAKING AND USING THEM

CROSS-REFERENCE TO RELATED APPLICATIONS

This application claims benefit under 35 U.S.C. § 119(e) of provisional application U.S. Ser. No. 60/495,634 filed Aug. 14, 2003. The contents of this application is incorporated herein by reference.

TECHNICAL FIELD

The present invention relates to novel calcium channel DNA and protein compositions, and to the expression and production of these compositions in cell lines for use in evaluating calcium channel function and identifying agonists/antagonists for these channels.

BACKGROUND ART

Voltage-gated calcium channels are a heterogeneous family of membrane proteins, which respond to depolarization by opening a calcium-selective pore through the plasma membrane. The influx of calcium into cells mediates a wide variety of cellular and physiological responses including excitation-contraction coupling, hormone secretion and gene expression. In neurons, calcium entry directly affects membrane potential and contributes to electrical properties such as excitability, repetitive firing patterns and pacemaker activity. Calcium entry further affects neuronal function by directly regulating calcium-dependent ion channels and modulating the activity of enzymes such as protein kinase C and calcium-dependent endent calmodulin-dependent protein kinase II. An increase in calcium concentration at the presynaptic nerve terminal triggers the release of neurotransmitters. Calcium entry also plays a role in neurite outgrowth and growth cone migration in developing neurons and has been implicated in long-term changes in neuronal activity.

In addition to the variety of normal physiological functions mediated by calcium channels, they are also implicated in a number of human disorders. Recently, mutations identified in human and mouse calcium channel genes have been found to account for several disorders including, familial hemiplegic migraine, episodic ataxia type 2, cerebellar ataxia, absence epilepsy and seizures. (Fletcher, C. F., et al., *Cell* (1996) 87:607–617; Burgess, D. L., et al., *Cell* (1997) 88:385–392; Ophoff, R. A., et al., *Cell* (1996) 87:543–552; Zhuchenko, O., et al., *Nature Genetics* (1997) 15:62–69. The clinical treatment of some disorders has been aided by the development of therapeutic calcium channel modulators or blockers. (Janis, R. J., et al., *Calcium Channels: Their Properties, Functions, Regulation and Clinical Relevance* (1991) CRC Press, London).

Native calcium channels have been classified by their electrophysiological and pharmacological properties as either high voltage-activated (L, N, P, and Q types) or low voltage-activated channels (T-type). R-type channels have biophysical properties similar to both high and low voltage-activated channels. (For reviews see McCleskey, E. W., et al., *Curr. Topics Membr.* (1991) 39:295–326, and Dunlap, K., et al., *Trends Neurosci.* (1995) 18:89–98.) T-type channels are a broad class of molecules that transiently activate at negative potentials and are highly sensitive to changes in resting potential. The L, N, P and Q-type channels activate at more positive potentials and display diverse kinetics and voltage-dependent properties. There is some overlap in biophysical properties among the high voltage-activated channels, consequently pharmacological profiles are useful to further distinguish them. L-type channels are sensitive to dihydropyridine (DHP) blockers, N-type channels are blocked by the *Conus geographus* peptide toxin, ω-conotoxin GVIA, and P-type channels are blocked by the peptide ω-agatoxin IVA from the venom of the funnel web spider, *Agelenopsis aperta*. A fourth type of high voltage-activated $Ca^{2+}$ channel (Q-type) has been described, although whether the Q- and P-type channels are distinct molecular entities is controversial (Sather, W. A., et al., *Neuron* (1993) 11:291–303; Stea, A., et al., *PNAS* (1994) 91:10576–10580), and it has been suggested that they result from alternative splicing of a single gene (Bourinet, et al., "Phenotypic variants of P- and Q-type calcium channels are generated by alternative splicing of the $α_{1A}$ subunit gene." *Nature Neuroscience* (1999) 2:407–415. Conductance measurements of several types of calcium channels have not always fallen neatly into any of the above classes and there is variability of properties even within a class, suggesting that additional calcium channels subtypes remain to be classified.

Biochemical analyses show that neuronal calcium channels are heterooligomeric complexes consisting of three distinct subunits ($α_1$, $α_2δ$ and $β$) (reviewed by De Waard, M., et al., *Ion Channels, Volume* 4, (1997) edited by Narahashi, T., Plenum Press, New York). The $α_1$ subunit is the major pore-forming subunit and contains the voltage sensor and binding sites for calcium channel blockers. The mainly extracellular $α_2$ is disulphide-linked to the transmembrane $δ$ subunit. Both are derived from the same gene and are proteolytically cleaved in vivo. The $β$ subunit is a nonglycosylated, hydrophilic protein with a high affinity of binding to a cytoplasmic region of the $α_1$ subunit. A fourth subunit, $γ$, is unique to L-type Ca channels expressed in skeletal muscle T-tubules. The isolation and characterization of γ-subunit-encoding cDNA's is described in U.S. Pat. No. 5,386,025, which is incorporated herein by reference.

Molecular cloning has revealed the DNA sequence and corresponding amino acid sequences of seven different types of $α_1$ subunits ($α_{1A}$, $α_{1B}$, $α_{1C}$, $α_{1D}$, $α_{1E}$, $α_{1F}$ and $α_{1S}$) and four types of $β$ subunits ($β_1$, $β_2$, $β_3$ and $β_4$) (reviewed in Stea, A., et al., *Handbook of Receptors and Channels* (1994) Edited by R. A. North, CRC Press). PCT Patent Publication WO 95/04144, which is incorporated herein by reference, discloses the sequence and expression of $α_{1E}$ calcium channel subunits. More recently, several $α_1$ subunits corresponding to the low voltage gated T-type calcium ion channel have been cloned. Descriptions of these cloned $α_1$ subunits may be found, for example, in PCT publications WO 98/38301 and WO 01/02561 as well as in U.S. Pat. Nos. 6,309,858 and 6,358,706, all incorporated herein by reference.

The different classes of $α_1$ and $β$ subunits have been identified in a variety of mammals including rat, rabbit and human, and share a significant degree of amino acid conservation across species—for example see:

For $β$: Castellano, A., et al., *J. Biol. Chem.* (1993) 268:3450–3455;
Castellano, A., et al., *J. Biol. Chem.* (1993) 268: 12359–12366;
Perez-Reyes, E., et al., *J. Biol. Chem.* (1992) 267: 1792–1797;
Pragnell, M., et al., *FEBS Lett.* (1991) 291:253–258;
For $α_1$: Dubel, S. J., et al., *Proc. Natl. Acad. Sci. USA* (1992) 89:5058–5062;
Fujita, Y., et al., *Neuron* (1993) 10:585–598;
Mikami, A., et al., *Nature* (1989) 340:230–233;

Mori, Y., et al., *Nature* (1991) 350:398–402;

Snutch, T. P., et al., *Neuron* (1991) 7:45–57;

Williams, M. E., et al., *Science* (1992) 257:389–395;

Both α & β: Soong, T. W., et al., *Science* (1993) 260: 1133–1136;

Tomlinson, W. J., et al., *Neuropharmacology* (1993) 32:1117–1126;

Williams, M. E., et al., *Neuron* (1992) 8:71–84.

In some expression systems the $\alpha_1$ subunits alone can form functional calcium channels although their electrophysiological and pharmacological properties can be differentially modulated by coexpression with any of the four β subunits. Until recently, the reported modulatory affects of β subunit coexpression were to mainly alter kinetic and voltage-dependent properties. More recently, it has been shown that β subunits also play crucial roles in modulating channel activity by protein kinase A, protein kinase C and direct G-protein interaction. (Bourinet, E., et al., *EMBO J.* (1994) 13:5032–5039; Stea, A., etal., *Neuron* (1995) 15:929–940; Bourinet, E., etal., *Proc. Natl. Acad Sci.* (USA) (1996) 93:1486–1491.)

Genes have been identified that encode four different but homologous $\alpha_2\delta$ subunits. The first subunit identified was $\alpha_2\delta$-1 in rabbit skeletal muscle. Five tissue-specific splice variants exist (Angelotti, T., et al., *FEBS Lett.* (1996)397: 331–337). $\alpha_2\delta$-2, -3 and -4 have been identified recently in human and mouse (Klugbauer, N., et al., *J. Neuroscience* (1999) 19(2):684–691; Qin, N., et al., *Mol. Pharmacol.* (2002) 62(3):485–496). These $\alpha_2\delta$ subunits share 30% to 56% amino acid sequence identity with the $\alpha_2\delta$-1 subunit as well as several structural motifs, such as similar hydrophobicity profiles, glycosylation sites and cysteine residues. $\alpha_2\delta$-1 and $\alpha_{2\delta}$-2 subunits are expressed in many tissues including the brain and heart, while $\alpha_2\delta$-3 is only found in the brain. $\alpha_2\delta$-4 is distributed in certain cell types of the pituitary, adrenal gland, colon and fetal liver. $\alpha_2\delta$-2 has been proposed as a tumor suppressor gene, and the mouse homolog is a candidate for the ducky epileptic phenotype (Gao, B., et al., *J. Biol. Chem.* (2000) 275(16): 12237–12242).

In general, the $\alpha_2\delta$ subunit does not function alone as a calcium ion channel, but rather is used in combination with the $\alpha_1$ subunit and optionally β, and in the case of L-type subunits, optionally a γ subunit.

The $\alpha_2\delta$-1 subunit increases the current density of calcium channels by increasing the amount of functional channel at the cell surface and enhances dihydropyridine binding to L-type channels and ω-conotoxin GVIA to N-type channels (Brust, P. F., et al., *Neuropharmacology* (1993) 32(11): 1089–1102; Felix, R., et al., *J. Neurosci.* (1997) 17(18): 6884–6891). $\alpha_2\delta$-2 and $\alpha_2\delta$-3 significantly enhance and modulate the current through a number of HVA and LVA channels (Hobom, M., et al., *Eur. J. Neurosci.* (2000) 12(4):1217–1226). Gabapentin, an antiepileptic, has been shown to bind to $\alpha_2\delta$-1 and $\alpha_2\delta$-2 but not to $\alpha_2\delta$-2 but not to $\alpha_2\delta$-3 (Marais, E., et al., *Molec. Pharmacol.* (2001) 59(5):1243–1248).

DISCLOSURE OF THE INVENTION

The materials and methods of the present invention add to the repertoire of $\alpha_2\delta$ functional subunits previously known. To applicants' knowledge, the only source of nucleic acid molecules which encode calcium ion channels have been based on the structures of these channels in mammalian systems. The present invention describes a new class of such materials and compositions that are characteristic of avian counterparts.

Thus, in one aspect, the invention is directed to isolated nucleic acid molecules which contain a nucleotide sequence that encodes a protein having the functional characteristics of $\alpha_2\delta$ protein and has an amino acid sequence at least 85% identical to that shown in SEQ ID NO:2, or to a functional portion thereof. In another aspect, the invention relates to the $\alpha_2\delta$ subunits themselves in isolated form that have an amino acid sequence at least 85% identical to SEQ ID NO:2 or a fragment of said sequence which retains the activity of this subunit. The invention is also directed to recombinant materials and methods for production of this protein and displaying it on cells. When displayed on cells which also produce, contain and display at least $\alpha_1$ subunits, the $\alpha_2\delta$ subunit of the invention in combination with the $\alpha_1$ subunit provide active calcium ion channels which can be used to identify agonists and antagonists of calcium ion channel activity.

In other aspects, the invention is directed to nucleic acid probes that permit recovery of additional $\alpha_2\delta$ encoding nucleic acids from avian systems and which permit the detection of expressed mRNA encoding the $\alpha_2\delta$ protein. In addition, antibodies which are immunospecific for the $\alpha_2\delta$ proteins of the invention can be used to map the distribution of this protein in cells and tissues.

MODES OF CARRYING OUT THE INVENTION

Figure 1:
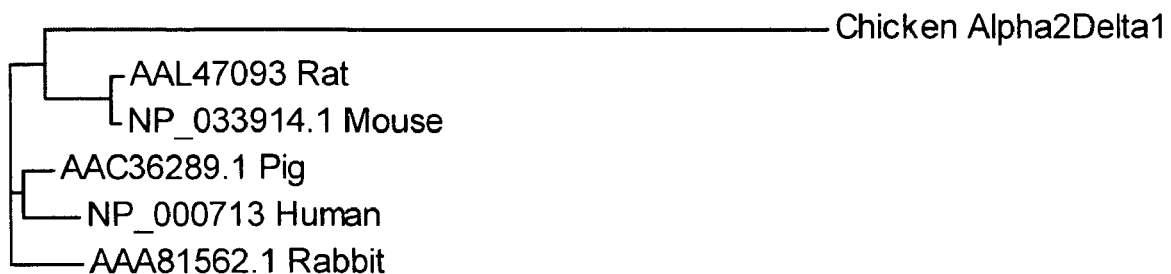
FIG. 1 is a schematic diagram of the evolutionary relationships between $\alpha_2\delta$-1 subunits in various species.
Figure 2A:
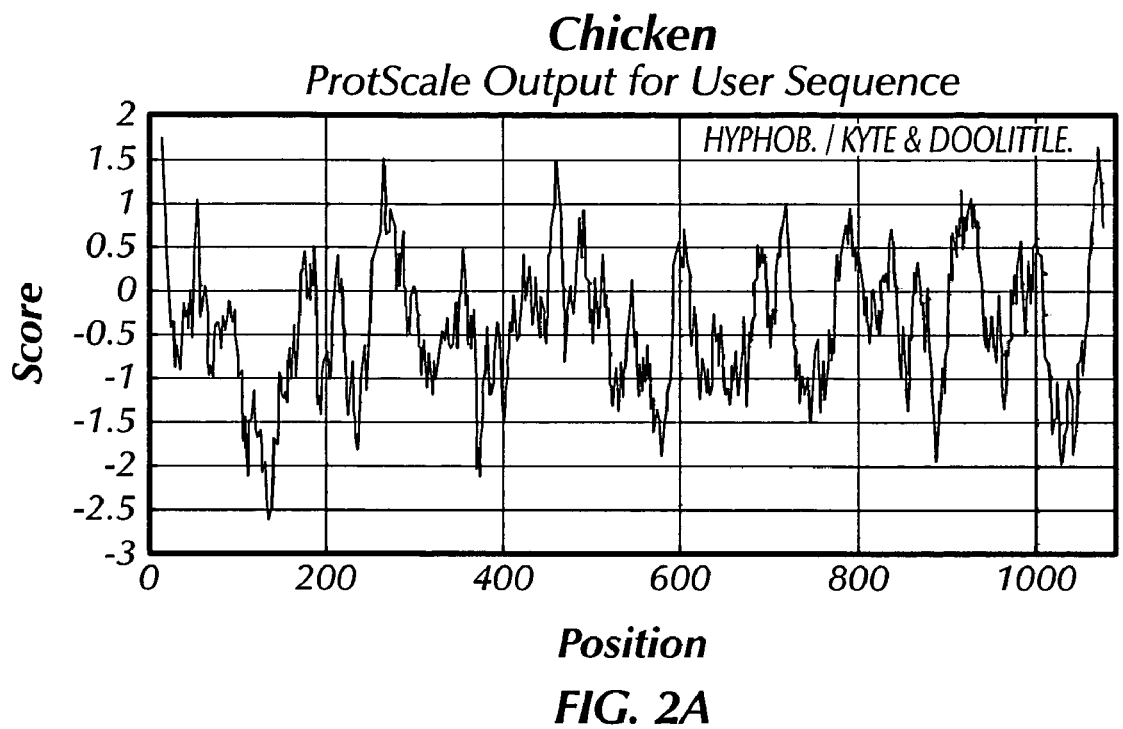
FIG. 2A–C shows a comparison of hydrophobicity plots for amino acid residues of the chicken, human and rat calcium channel $\alpha_2\delta$-1 subunits.
Figure 2B:
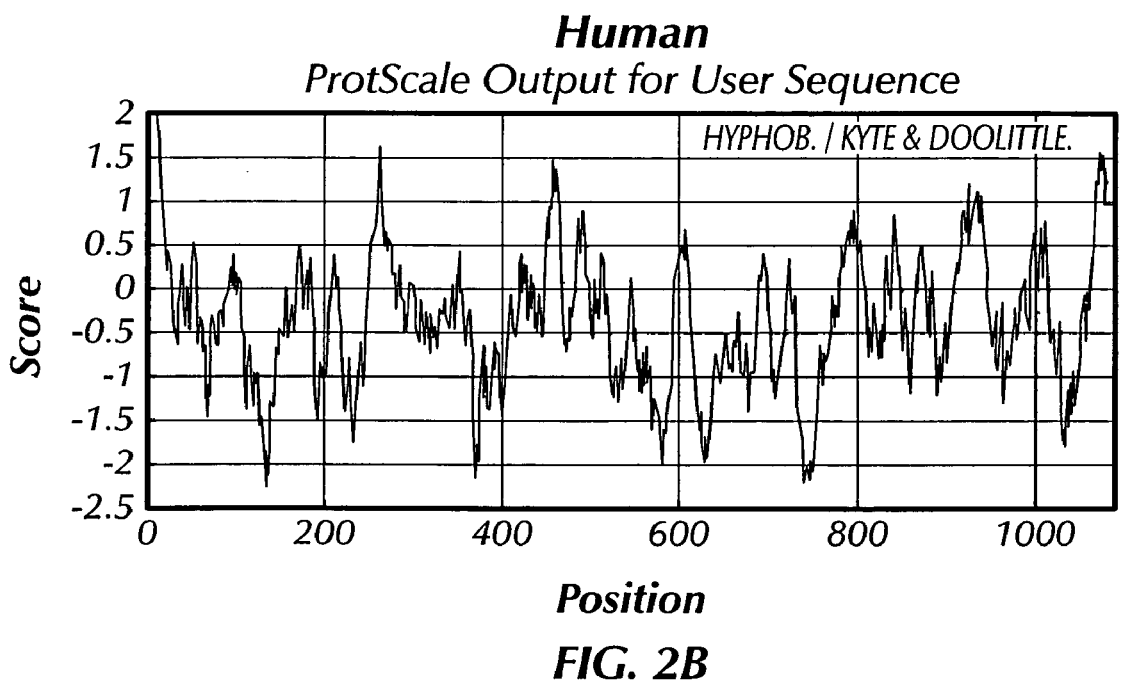
Figure 2C:
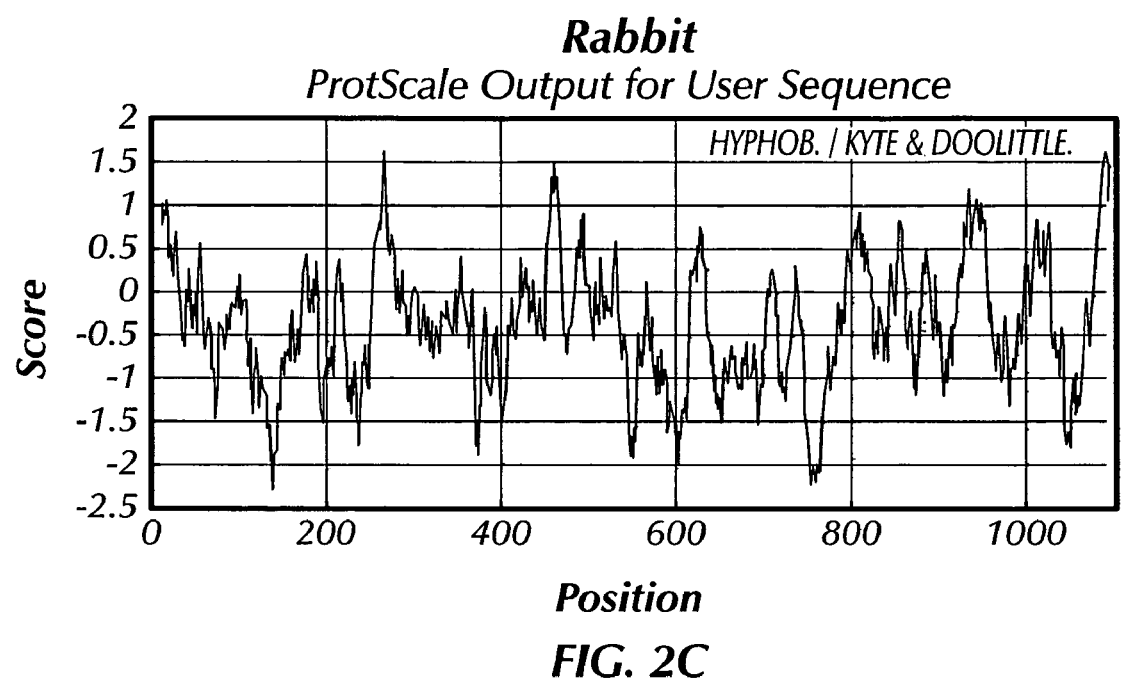

The present invention provides a new class or group of $\alpha_2\delta$ functional subunits, which differ in structure from the corresponding mammalian subunits known in the art. As described in the Background section above, it is understood that $\alpha_2\delta$ subunits alone do not mediate transport calcium across the cellular membrane; however, they increase the current density of calcium channels by increasing the amount of functional channel at the cell surface and enhancing binding of certain ligands. Typically, the $\alpha_2\delta$ subunits require the presence of an $\alpha_1$ subunit, and are preferably expressed or assessed in the additional presence of β type subunits. If the $\alpha_1$ subunit employed is from an L-type channel, the additional presence of a γ subunit is also desirable.

As described in the Background section above, there appear to be four specific types of this subunit, $\alpha_2\delta$-1, $\alpha_2\delta$-2, $\alpha_2\delta$-3 and $\alpha_2\delta$-4. While in their native expression, each of these types may preferentially be associated with a particular class of calcium ion channel (e.g., L, P/Q, N, T and the like), each of these subunits is functional when in association with any $\alpha_1$ subunit with the optional addition of any type of β subunit. Although the text herein refers to $\alpha_2\delta$ because this is the protein encoded by a single gene, the encoded protein is hydrolyzed after translation into the $\alpha_2$ and $\delta$ portions; the $\alpha_2$ portion is mostly extracellular and is disulfide linked to the $\delta$ subunit which remains in the cell membrane. By "functional $\alpha_2\delta$ subunit" is meant the entire amino acid sequence encoded by the gene or any portion thereof which, when associated with an $\alpha_1$ subunit and optionally $\beta$ subunit enhances the density of current flow in the calcium ion channel thus created. Thus, is it understood that small numbers of amino acids, e.g., 10–15 or 20 amino acids might be removed from each of the $\alpha_2$ and/or $\delta$ portions while the remainder of the sequence retains functionality as described above. Thus, a "functional portion of the $\alpha_2\delta$ subunit" refers to these truncated forms.

A compound, such as a nucleic acid molecule or a protein is referred to as "isolated" when it is removed from its natural environment. It may or may not be pure. "Isolated" simply means that the molecule is in a context where it is not found in nature. For example, a nucleic acid comprising a particular nucleotide sequence is "isolated" when contained in a recombinant DNA molecule coupled to additional nucleotide sequences with which it is not normally associated. Similarly, the "protein" is isolated when it is not in the context of its native cell. "Isolated" $\alpha_2\delta$ subunits, for example, are frequently found in the context of a displayed calcium ion channel in a heterologous cell, which has been modified to produce this protein.

Although in some instances, an $\alpha_1$ subunit displayed at a cellular surface may be functional at some level in the absence of additional subunit types, the presence of the $\alpha_2\delta$ subunit greatly enhances the current density when the channel is activated. Accordingly, the production of $\alpha_2\delta$ subunits for display on cells, which also display at least $\alpha_1$ subunits is important for use in screening assays to identify compounds that modulate the activity of the calcium ion channel.

The particular class of $\alpha_2\delta$ subunits that constitute the present invention have an amino acid sequence at least 85% identical to that shown in SEQ ID NO:2 or at least 85% identical to a portion of that sequence that retains its functionality. Other embodiments are characterized by amino acid sequences that are 90% identical, 95% identical, 98% identical, 99% identical or completely identical to SEQ ID NO:2 or a functional fragment.

The amino acid sequence set forth as SEQ ID NO:2 is specifically an $\alpha_2\delta$-1 calcium channel subunit which is present in the brain and spinal cord of the White Leghorn chicken. SEQ ID NO:2 is 1,087 amino acids in length and has a molecular weight of 123 kD. It is encoded by a nucleotide sequence containing 3,261 base pairs which is contained in the 3,684 base pair sequence shown as SEQ ID NO:1. Table 1 shows the percentage identity of the open reading frame contained in SEQ ID NO:1 and the amino acid sequence shown in SEQ ID NO:2 with respect to mammalian $\alpha_2\delta$-1 sequences.

TABLE 1

| $\alpha_2\delta$-1 DNA sequence Identities: compared across Open Reading Frame | |
|---|---|
| Chicken vs Pig | 78% |
| Chicken vs Human | 77.8% |
| Chicken vs Rat | 76.3% |
| Chicken vs Mouse | 76.9% |
| Chicken vs Rabbit | 75.8% |
| $\alpha_2\delta$-1 amino acid sequence identities | |
| Chicken vs Pig | 80.3% |
| Chicken vs Human | 79.7% |

TABLE 1-continued

| Chicken vs Rat | 79.9% |
|---|---|
| Chicken vs Rabbit | 78.5% |
| Chicken vs Mouse | 80.2% |

As shown, this representative avian subunit represents a new class, as compared to mammalian sequences.

An examination of the nucleotide sequence contained in SEQ ID NO:1 shows a Kozak consensus translation initiation sequence at the first start codon and two possible poly-A signal sites at the 3' untranslated region as predicted by a Hamming Clustering analysis using a six unit pattern length. The encoded protein is predicted to have a 20 amino acid signal peptide and a hydrophobicity profile similar to that of the mammalian $\alpha_2\delta$ subunits. There are 19 conserved cysteine amino acids in the chicken $\alpha_2\delta$ protein that correspond to those in the mammalian $\alpha_2\delta$ proteins.

When the $\alpha_2\delta$ protein is displayed on cells in the presence of or coexpressed with the $\alpha_1$ subunit of any calcium ion channel and optionally as well, a $\beta$ subunit, the resulting cells are useful in identifying compounds that modulate the activity of the channel. The nature of the channel is effectively determined by the nature of the $\alpha_1$ subunit, but in all cases the $\alpha_2\delta$ subunit enhances current flux so that a more accurate measurement can be made. A malfunction of calcium ion channels is associated with a number of conditions; depending on the nature of the channel. For example, defects in calcium channels are associated with conditions including, but not limited to: epilepsy, migraine, ataxia, schizophrenia, hypertension, arrhythmia, angina, depression, small lung carcinoma, Lambert-Eaton syndrome.

Compounds identified that agonize or antagonize the various calcium ion channels are thus suitable drug candidates for treatment of these conditions. It is understood that not all agonists and antagonists thus identified will ultimately become successful drugs; however, the identification of a subpopulation of the millions of molecules that would otherwise be candidates represents a giant step toward development of a suitable drug.

While the required display of the calcium ion channels, which include the $\alpha_2\delta$ subunits of the invention may be effected in a variety of animal cells, exemplary cells include *Xenopus* oocytes or mammalian cells such as human embryonic kidney (HEK 293) cells as described in PCT Publication No. WO 96/39512 incorporated herein by reference and Ltk cells as described in U.S. Pat. No. 5,386,025 incorporated herein by reference. Transfection into host cells is accomplished by, for example, microinjection, lipofection, electroporation, calcium phosphate (glycerol shock) or particle-mediated gene transfer.

Mammalian cell lines stably expressing the $\alpha_2\delta$ are, for example, prepared by transfecting expression vectors encoding $\alpha_2\delta$ calcium channel into mammalian cells such as HEK 293 and selecting for antibiotic resistance encoded by the expression vector, for example, pBK-RSV or pcDNA with a selectable marker (InvitroGen, San Diego, Calif.). The vectors are transfected into HEK 293 cells by calcium phosphate co-precipitation or lipofection or electroporation or any other method according to well known procedures (*Methods in Enzymology, Volume 185, Gene Expression Technology* (1990) Edited by Goeddel, D. V.). The $\alpha_2\delta$ subunit is transfected alone, or in combination with other calcium channel subunit cDNA's, such as the $\alpha_{1B}$ and $\beta_{1b}$ subunits, either in a similar expression vector or other type of vector using different selectable markers. The additional subunits may be of chicken, mammalian, or other animal origin. Transfected cells are typically incubated for 4–24 hrs under DNA transfection conditions at 37° C., 5% $CO_2$, then placed in nonselective medium for an additional 24 hrs. The cells are trypsinized and plated at low density in selective medium containing Geneticin (G418) between 600 to 800 μg/ml and/or Zeocin between 50 to 100 μg/ml. After 10–16 days in selective medium, cells that are resistant to G418 and/or Zeocin grow as visible colonies, which are harvested as isolated colonies by the pipette technique or using standard cloning rings. Isolated cell colonies are then expanded to make frozen stocks of cells and to determine the level of $\alpha_2\delta$ subunit expression. Southern blotting can be used to detect the integration of the subunit into the cell genome or the presence of the plasmid episomally, and the number of copies present $\alpha_2\delta$ expression levels for the cell lines are determined using standard gene expression methods such as Northern blotting, RNase protection, reverse-transcriptase PCR, and Western blotting.

The functional detection of calcium channels containing $\alpha_2\delta$ subunits of the invention in stably transfected cells can be examined electrophysiologically, such as by whole patch clamp or single channel analysis (see above). Other means of detecting functional calcium channels include the use of radiolabeled $^{45}Ca$ uptake, or fluorescence spectroscopy using calcium sensitive dyes such as FURA-2.

The resulting cell lines expressing functional calcium channels comprising the $\alpha_2\delta$ subunit of the invention and at least an $\alpha_1$ subunit can then be used as test compounds for pharmacological activity with respect to these calcium channels as set forth above. Such screening can be carried out using several available methods for evaluation of the interaction, if any, between the test compound and the calcium channel. One such method involves the binding of radiolabeled agents that interact with the calcium channel and subsequent analysis of equilibrium binding measurements including but not limited to, on rates, off rates, Kd values and competitive binding by other molecules. Another method involves screening for the effects of compounds by electrophysiological assay whereby individual cells are impaled with a microelectrode and currents through the calcium channel are recorded before and after application of the compound of interest. Another method, high-throughput spectrophotometric assay, utilizes loading the cell lines with a fluorescent dye sensitive to intracellular calcium concentration and subsequent examination of the effects of compounds on the ability of depolarization by potassium chloride or other means to alter intracellular calcium levels.

Compounds that are found to modulate the calcium ion channels, wherein the $\alpha_2\delta$ subunit of the invention is used to enhance the signal, and thereby increase the accuracy and reproducibility of results, are useful in treating conditions associated with defects in performance of these channels. The nature of these conditions depends on the type of calcium ion channel involved; but since the $\alpha_2\delta$ subunit of the invention enhances the signal for all types of calcium ion channels, it is useful in detecting compounds for a wide variety of conditions. Defects in calcium channels are associated with conditions including, but not limited to: epilepsy, migraine, ataxia, schizophrenia, hypertension, arrhythmia, angina, depression, small lung carcinoma, Lambert-Eaton syndrome.

Detection of Calcium Ion Channel Expression

Expression of calcium ion channels that contain the $\alpha_2\delta$ subunit of the invention can be detected at the mRNA or protein level. The expression detection assays can be conducted as, or modified to be conducted as, in vitro or in vivo assays, and may be either cell-free (e.g., in vitro binding assays using polynucleotides isolated from or produced from nucleic acid of a biological sample) or cell-based (e.g., screening of whole cells for expressing the $\alpha_2\delta$ subunits of the invention). In general, all assays are conducted under conditions, and for a period of time, sufficient to allow for specific binding of a $\alpha_2\delta$ probe specific to the $\alpha_2\delta$ of the invention (e.g., nucleic acid probe, antibody probe) to provide for detection of the subunit probe target at a detectable level above background. The assays can include various positive and/or negative controls, the nature of which will be readily apparent to the ordinarily skilled artisan.

Any suitable qualitative or quantitative methods known in the art for detecting specific $\alpha_2\delta$ mRNAs of the invention can be used to detect or quantitate expression. For example, the invention $\alpha_2\delta$ mRNA in cells can be measured by various techniques known in the art including, but not limited to, S1 nuclease analysis, ribonuclease protection assay, primer extension assay, RNA blot analysis (e.g., Northern and/or slot blot hybridization) and amplification techniques including reverse transcriptase-PCR (RT-PCR). In addition, expression can be assessed in histological assays. For example, the $\alpha_2\delta$ RNA of the invention can be detected by in situ hybridization in tissue sections, using methods that detect single base pair differences between hybridizing nucleic acid and other methods well known in the art.

Typically northern blot of total mRNA or fractionated RNA or RT-PCR are employed. The Northern Blot or RT-PCR product is hybridized with a cDNA probe of SEQ ID NO:1 or portions of SEQ ID NO:1 unique to this sequence or its complement, under conditions of high stringency (50% formamide in Church buffer @+50° C. or 65° C. in aqueous buffer, Church and Gilbert's) and washed at high stringency (0.5× SSC/0.1% SDS–0.1× SSC/0.1% SDS, 65–68° C.). Typically, the probes contain at least 12 consecutive nucleotides derived from SEQ ID NO:1 or the complement thereof. The probes are portions that are distinctive regions—i.e., comprise at least one nucleotide difference from $\alpha_2\delta$ subunits other than those of the invention. When mRNA encoding the $\alpha_2\delta$ subunits of the invention is present, its presence and amount can thus be detected.

Nucleic acid probes can be prepared using routine methods, including automated oligonucleotide synthetic methods. For use of such probes, the biological sample to be analyzed may be treated, if desired, to extract the RNA. The resulting RNA from the sample may be subjected to gel electrophoresis or other size separation techniques; alternatively, the RNA sample may be dot blotted without size separation. The probes are usually labeled with a detectable label. Suitable labels, and methods for labeling probes are known in the art, and include, for example, radioactive labels incorporated by nick translation or kinasing, biotin, fluorescent probes, and chemiluminescent probes. The RNA extracted from the sample is then treated with the labeled probe under hybridization conditions of suitable stringency.

In addition to detecting mRNA production, the probes of the invention, as described above, can be used to recover nucleotide sequences encoding $\alpha_2\delta$-2 subunits from other animals including avians. The probes may be used with respect to cDNA libraries or genomic libraries derived from other species, and are tested for hybridization under the high stringency conditions described above.

For detection at the protein level, it is convenient to produce antibodies to $\alpha_2\delta$ proteins of the invention. As defined above, these proteins have at least 85% identity to SEQ ID NO:2. The antibodies are immunospecific to this protein if they immunoreact detectably more strongly to the $\alpha_2\delta$ subunits of the invention as compared to other proteins, including $\alpha_2\delta$ proteins of the prior art. The antibodies may be polyclonal, monoclonal, single-chain recombinant, and the like. Methods for preparation of such antibodies, including antibodies designed to be compatible with individual species such as humanized antibodies are well known. It is also understood that the term "antibodies" includes immunospecific fragments thereof, such as $F_{ab}$, $F_{ab'}$, and the like. As mentioned above, single-chain $F_v$ antibodies also represent useful fragments.

These antibodies can be used to detect the production of any calcium channel, which includes the $\alpha_2\delta$ subunit on histological sections or tissue extracts. Expression and display on recombinant cells can also be detected using these antibodies. Standard methods for labeling and detecting the antibody complexes are employed. The antibody in the immunoassays for detection of the $\alpha_2\delta$ protein of the invention may be provided on a support (e.g., solid or semi-solid); alternatively, the protein in the sample can be immobilized on a support. Examples of supports that can be used are nitrocellulose (e.g., in membrane or microtitre well form), polyvinyl chloride (e.g., in sheets or microtitre wells), polystyrene latex (e.g., in beads or microtitre plates), polyvinylidine fluoride, diazotized paper, nylon membranes, activated beads, and Protein A beads. Bead-based supports are generally more useful for immobilization of the antibody in the assay.

In one embodiment, the biological sample contains cells (i.e., whole cells) and detection is by reacting the sample with labeled antibodies, performed in accordance with conventional methods. In general, antibodies that specifically bind $\alpha_2\delta$ protein of the invention are added to a sample, and incubated for a period of time sufficient to allow binding to an epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g., fluorescein, rhodamine, Texas red, and others). The absence or presence of antibody binding can be determined by various methods, including, but not limited to, flow cytometry of dissociated cells, microscopy, radiography, and scintillation counting. Any suitable alternative methods of qualitative or quantitative detection of levels or amounts of differentially expressed polypeptide can be used, for example ELISA, western blot, immunoprecipitation, radioimmunoassay, and the like.

The following examples are offered to illustrate but not to limit the invention.

EXAMPLE 1

Cloning the $\alpha_2\delta$-1 Calcium Channel Subunit

A. Initial Retrieval cDNA encoding avian $\alpha_2\delta$-1 subunit was generated from chicken mRNA by RT-PCR.

Degenerate sense and antisense primers for RT-PCR were designed based on the consensus DNA sequence of mammalian $\alpha_2\delta$ genes as follows:

```
1F,      5'gcctgctggcctigacictgacac3';

2F,      ccgtcactatcaagtcatgggtg;

R1,      5'ggtcayaiyagitagtgtctgctgccag3';
```

-continued

```
R2,         5'acaccaccicagtcigtataatcctc3';

3F,         5'agaggacctattcagtggatggc3';

R3,         5'caagccatccactgaataggtcctc3';

228/SIGF,   5'tcytcgitcgcgaagatggctgc3').
```

One-step RT-PCR and RT-PCR with chicken mRNA (Clontech) template, was used to amplify two overlapping fragments of the chicken $\alpha_2\delta$ subunit. A full-length chicken $\alpha_2\delta$ was made by amplifying the entire cDNA using PCR with the two overlapping (F3-R3) PCR fragments as template.

The full length PCR $\alpha_2\delta$ cDNA was inserted into the mammalian expression vector pBK-RSV (-lac p), transfected into HEK 293 cells and found to enhance N-type channel activity as measured by electrophysiology.

B. Confirmation

The accuracy of the $\alpha_2\delta$ PCR clone was confirmed by screening a chicken spinal cord lambda cDNA library (Stratagene), using standard procedures. Bacteria were infected with recombinant lambda phage containing this cDNA library and the amplified lambda DNA was immobilized onto nylon filters (Hybond-N, Amersham Pharmacia biotech). Using a restriction enzyme digest with Nde I and Fsp I two cDNA probes were made from the 3' PCR fragment of the chicken PCR clone and $[\alpha^{32}P]$ dCTP radiolabeled using the High Prime Kit (Roche). Approximately 300,000 plaque forming units (pfus) were screened with the radiolabeled probes using moderate hybridization (55° C.) and washing conditions (55° C., 0.5× SSC). Bacteriophage that hybridized to the chicken $\alpha_2\delta$ radiolabeled probe were detected by exposing the membranes to autoradiography. Positive clones were purified by sequential rounds of screening and the phagemid cDNA isolated by in vivo excision using the ExAssist helper phage with SOLR Strain *E. coli* according to the manufacturer's instructions.

Three positive clones were sequenced and found to contain cDNA fragments of the chicken $\alpha_2\delta$ subunit 1 (range 2.8–0.9 Kb). Four amino acid differences were identified in this region of the chicken $\alpha_2\delta$-1 library clones compared to the initial PCR clone.

Library clone 2112 is 2782 bp, commencing 980 bp downstream of the translational start codon. In order to confirm the first 980 bp of the original PCR clone (see above), this region was amplified in two parts from the chicken spinal cord library using nested PCR with a T3 sense primer to the pBluescript SK vector or the sense primer 228/SIGF and antisense primers:

```
R4,      5'ggatgaagtagcacatacccattagg3';

R8,      gtagtatccatttggacaaagcgt3';

R11,     aatactggtctgattctctggctgc3'
``` to the original PCR clone. Sequencing of a number of these two overlapping fragments showed 100% identity to the original PCR clone amplified from mRNA.

C. Construction of Full-Length cDNA

A full-length $\alpha_2\delta$ clone was constructed in the cloning vector pBlue KS+ by ligation of a BsaA I/Hind III fragment of clone 2112 (cDNA library) and a Not I/BsaA I fragment of the RT-PCR cDNA. For expression in mammalian cell lines the full-length chicken α₂δ was excised from pBlue KS+ by restriction enzyme digest with Not I/Dra I or Not I/Hind III and ligated into pBK-RSV (-lac p). The construct was transfected into HEK 293 or HEK 293 tsA 201 cells with equimolar concentration vectors for expression of the subunits $α_{1B}$ (N-type calcium channel) and $β_{1b}$, using lipofectamine (Gibco/Invitrogen) according to the manufacturer's instructions. pEGFP is included in the transfected DNA at 3–5 times less the molar concentration to detect transfected cells and to determine the efficiency of transfection. Transfected cells were incubated at 37° C., 5% $CO_2$, for 6–24 hrs and then placed at 29° C., 5% $CO_2$.

These cells are tested for calcium channel activity by electrophysiology. The full-length clone has SEQ ID NO:1:

Full-length Chicken α₂δ-1 Calcium Channel Subunit

```
   1 GATCTTCGAT CAGGAAGATG GCTGCTGGCT GGCTGCTGGT CTTTAGCCTG ACACTTTTCC
  61 AGTCTCTGGT GATGAACCAC TCGTCGGAGG GCCCGTTCCC TTCGCCCACC ACGATAAAGT
 121 CATGGGTAGA TAAGATGCAA GAGGACCTCA TAACATTGGC ACGAACTGCA AGTGGAGTGG
 181 AACAGCTTGC TGCGATATAT TTGAAAAACA AAGATTTGTA TACCGTAGAA GCCAACAATC
 241 CTCGTCAGCT AGTGGAAATT GCAGCCAGAG ACATTGAAAA ACTTCTGAGC AACAGATCTA
 301 AGGCTTTGGT GCGCCTCGCT AAAGAAGCAG AGAAGTACCA AGCATCACAT CAGTGGAGGG
 361 ATGAGTTTGG GAATAATGAT ATAATCTATT ACAATGCAAA AGATGATCAG AATGATCCTG
 421 AAAAGAATGA CACTGAATCT GGCAGCCAGA GAATCAGACC AGTATTTGAA GAAGATCCTG
 481 TTTTCCGACG GCAAACGTCT TACCAACATG CAGCAGTTCA CATACCAACA GATATTTATG
 541 AAGGCTCAAC AATAGTGTTA AATGAACTCA ATTGGACTGC AGCACTGGAT GATGTATTCA
 601 AGCGGAACAG AGAAGAAGAC CCCACTTTAT TATGGCAAGT TTTTGGTAGT GCAACTGGCC
 661 TCGCTAGGTA TTACCCAGCT TCTCCATGGG TAGATAATAG TCGAACTCCA AACAAAATAG
 721 ATCTATATGA TGTTCGCAGA AGACCATGGT ATATCCAAGG AGCTGCATCT CCCAAAGACA
 781 TGCTTATTTT AGTTGATGCG AGCGGGAGTG TGAGTGGATT GACGCTGAAG CTGATCCGCA
 841 CATCGGTCAT TGAGATGTTA GAGACCTTGT CTGATGATGA CTTTGTGAAT GTAGTTTCAT
 901 TTAATAATAA TGCTCAGAAC GTCAGTTGCT TTAATCATCT TGTCCAAGCT AATGTGAGGA
 961 ACAAGAAGAA GCTGAAGGAA GCTGTGGATA AAATCTCTGC TAAAGGAATT ACTGATTACA
1021 AAAAAGGCTT TAGCTACGCT TTTGAACAGC TGCTCAATCA CAGCGTTTCT AGAGCTAACT
1081 GCAATAAGAT TATAATGTTG TTTACGGATG GTGGTGAGGA AAGAGCACAA GAAATATTCC
1141 ATAAATATAA TGAAGACAAA AAAGTACGTG TGTTCACATT TTCTGTTGGT CAACATAATT
1201 ATGACAAAGG ACCTATACAG TGGATGGCCT GTGAAAATAA AGGTTATTAT TATGAAATTC
1261 CATCCATTGG AGCCATAAGA ATAAACACCC AGGAATATCT GGACGTTTTG GGAAGGCCAA
1321 TGGTGTTAGC TGGTGAGAAA GCCAAACAGG TCCAATGGAC AAATGTCTAT CTGGATGCTC
1381 TGGAGCTGGG CCTTGTGATT ACAGGAACTC TGCCTGTCTT CAATCTAACA AAAGAACAAA
1441 ATGGAAAAAT AAATCAGCTG ATTCTTGGAG TAATGGGGGT TGATGTCTCT CTGGAAGATA
1501 TAAAAAAGCT GACACCTCGA TTTACGCTTT GTCCAAATGG ATACTACTTT GCAATTGATC
1561 CTAATGGGTA TGTGCTACTT CATCCAAATC TTCAACCAAA GAATCCTAAA TCCCAGGAGC
1621 CAGTAACACT GGATTTTCTA GATGCTGAAC TGGAAAATGA TATTAAAGTT GAGATTCGGA
1681 AAAAAATGAT AGATGGAGAA AGTGGAGAAA AAACATTTGA AACTCTGGTC AAGTCCCAAG
1741 ATGAGAGATA TATTGATAAA GGAAATCGAA CATATACATG GACTGCTGTG AATGGCACTG
1801 ATTACAGTTT GGCATTGGTG CTACCATCAT ACAGCTTTTA TTATATTAAA GCTAAAATAG
1861 AAGAACCAAT AACTCAAGCC AGATTGGAAA TCAAAAAGGA TTCAGAAACA CTGAAGATTG
1921 ATCATTTTGA TGAAGCTGGC TATACGTTTA TAGCACCAAG AGAATATTGT ACTGATGTAA
1981 AGAAATCAGA AAATAACACT GAATTTTTGT TAAATTTTAA TGAATTTATC GATAGAAATA
2041 CTCCAAGCAG TCCATCATGT AATACTGATA TGGTCATTAG AGTTCTGCTG GATGCAGGAT
```

-continued

```
2101 TTACAAATGA ACTTGCCCAA AATTATTGGA GTAAGCTGTA TCTTGATGGA GTTGTTGCGC
2161 AATTTGTTGT TACGGATGGT GGAATTACAA GAGTGTTCCC CAAAAGGGCA GGAGAAGATT
2221 GGTTGGAAAA TGCAGAAACT TATGAAGTCA GTTTCTATAA ACGGAGTTTA GATAATGACA
2281 ACTATATTTT CACAGCTCCA TACTACAACA AAAGCGGTGC CAATAGCTAT GAATCAGGTA
2341 TTATGGTAAG CAAGGCCGTG GAAATAACAA TTAATGGAAA ACTTCTGAAA CCTGCAGTTG
2401 TTGGAATAAA AATTGATGCA ATGAAATGGA TGGAAAATTT CACAACAACC ACAATCAAGA
2461 GCCTGTGCAA CAGTGAAATC TGTGGCTGTG AAAAAAACAG TATGCATGTG GACTGTGTTA
2521 TCCTTGATGA TGGTGGATTT CTTCTGATGT CAAATCGGGA TGAATATACC CACCAGATTG
2581 GAAGATTCTT TGGTGAAATT GACCCTGGCT TGATGAGAAA TTTAATTAAC ATGTCCCTGT
2641 ATGCCTTTAA CAAGTCATAT GACTATCAAT CAGTCTGTGA TCCTGAAGAA GAACCAAAGC
2701 AAGGAGCTGG ACTTCGTTCA GCTTATGTGC CTACAATAGC AGATATTTTG CAACTAGGAT
2761 GGTGGGCTTC AGCAGCTGCC TGGTCTATCT TACAGCAGCT CTTTTTGAGC TTGACTTTCC
2821 CACGTTTCCT TGAGGCAGCT GATATGGAAG ATGACGATTT CTCTACTGCT CTGCCTAAAA
2881 CAAGTTGTAT CACTGAGCAA ACTCAGTATT TCTTTGAAAA TGATGATAAA TCTTTTATTG
2941 GGATTGTAGA CTGCATCAAC TGTTCAAGAC TTTATCATGC AGAGAAGATT TCAAACACCA
3001 ATCTAGTATT CATTATTAGT GACAGCCAAC TGCTGTGCCG CTCCTGTGAT CCAAAGCCAC
3061 TGATGCAAGC AGAGAAGCCG GATGAAGGGC CAAATCCTTG TGAAATGGTC AAACAGCCCA
3121 GATACAGAAA AGGTCCCGAT GTCTGTTTTG ATGAAGCCAA ACAGGAAGAT TCGGCTGATT
3181 GCGGTGGTGC CTCTGGTTTG AGTCCATCAC TGTGGTCTAT GGTAGGAATT CAGTTGGTCC
3241 TGCTTTGGCT CTTATCTGGC AGCAGACACT ACCAGTTATG ACCTTGCTAA AATAAAACCT
3301 GCATAACTTA ATCAAGATCC AGCCAAAATG ACAGCCTCAG TTTCATTTTA AAAAGGGTCA
3361 GCTATTCAGG CAGCAGCAGA ACACCAATGC TCATGTCTGG TTATCATGCG TTGTGAGATT
3421 CATAAAGGCA CTCAAAATGG CTGCATATTG GAGTGTCAAT CCTTAAACGT ATGTGAATGC
3481 TGCATCATCT CTACCACCCA AACAGAATTC CGTACACATT TCATTGGGGA ATCTAAGATT
3541 TTTTGTCATT CATTTGTTGT TGTAATCTCA ATGACTTCAT GTAAAAGGGC TCCCCTGACC
3601 ATAGTGTATG TATATGATTT TCATTTATTT TAAGCTTTGG ATTTCTTGAA GATTTATATT
3661 CTTTTACATG AACATTTATT TATG
``` and the deduced amino acid sequence is SEQ ID NO:2:
Translated Chicken $\alpha_2\delta$-1 Amino Acid Sequence

```
  1 MAAGWLLVFS LTLFQSLVMN HSSEGPFPSP TTIKSWVDKM QEDLITLART ASGVEQLAAI
 61 YLKNKDLYTV EANNPRQLVE IAARDIEKLL SNRSKALVRL AKEAEKYQAS HQWRDEFGNN
121 DIIYYNAKDD QNDPEKNDTE SGSQRIRPVF EEDPVFRRQT SYQHAAVHIP TDIYEGSTIV
181 LNELNWTAAL DDVFKRNREE DPTLLWQVFG SATGLARYYP ASPWVDNSRT PNKIDLYDVR
241 RRPWYIQGAA SPKDMLILVD ASGSVSGLTL KLIRTSVIEM LETLSDDDFV NVVSFNNNAQ
301 NVSCFNHLVQ ANVRNKKKLK EAVDKISAKG ITDYKKGFSY AFEQLLNHSV SRANCNKIIM
361 LFTDGGEERA QEIFHKYNED KKVRVFTFSV GQHNYDKGPI QWMACENKGY YYEIPSIGAI
421 RINTQEYLDV LGRPMVLAGE KAKQVQWTNV YLDALELGLV ITGTLPVFNL TKEQNGKINQ
481 LILGVMGVDV SLEDIKKLTP RFTLCPNGYY FAIDPNGYVL LHPNLQPKNP KSQEPVTLDF
```

```
-continued

541 LDAELENDIK VEIRKKMIDG ESGEKTFETL VKSQDERYID KGNRTYTWTA VNGTDYSLAL

601 VLPSYSFYYI KAKIEEPITQ ARLEIKKDSE TLKIDHFDEA GYTFIAPREY CTDVKKSENN

661 TEFLLNFNEF IDRNTPSSPS CNTDMVIRVL LDAGFTNELA QNYWSKLYLD GVVAQFVVTD

721 GGITRVFPKR AGEDWLENAE TYEVSFYKRS LDNDNYIFTA PYYNKSGANS YESGIMVSKA

781 VEITINGKLL KPAVVGIKID ANKWMENFTT TTIKSLCNSE ICGCEKNSMH VDCVILDDGG

841 FLLMSNRDEY THQIGRFFGE IDPGLMRNLI NMSLYAFNKS YDYQSVCDPE EEPKQGAGLR

901 SAYVPTIADI LQLGWWASAA AWSILQQLFL SLTFPRFLEA ADMEDDDFST ALPKTSCITE

961 QTQYFFENDD KSFIGIVDCI NCSRLYHAEK ISNTNLVFII SDSQLLCRSC DPKPLMQAEK

1021 PDEGPNPCEM VKQPRYRKGP DVCFDEAKQE DSADCGGASG LSPSLWSMVG IQLVLLWLLS

1081 GSRHYQL*
```

EXAMPLE 2

Heterologous Expression of Chicken $\alpha_2\delta$-1 Calcium Channel Subunits A. Transient Transfection in Mammalian Cells Human embryonic kidney cells, HEK 293 (ATCC# CRL 1573) were grown in standard DMEM medium supplemented with 2 mM glutamine and 10% fetal bovine serum and transfected by a standard calcium-phosphate-DNA co-precipitation method or by lipofection with the full-length chicken $\alpha_2\delta$-1 calcium channel cDNA in the mammalian expression vector pBK-RSV (see Current protocols in Molecular Biology): alone or in combination with expression vectors encoding $\alpha_1$ and $\beta$ subunits, and with vectors expressing green fluorescent protein (GFP).

After an incubation period of 24 to 72 hrs, the culture medium was removed and replaced with an external recording solution containing (in mM) 5 BaCl, 129 CsCl, 1 MgCl$_2$, 10 HEPES, 10 glucose, pH 7.4 with CsOH. Whole-cell patch clamp recordings were made with an Axopatch 200B amplifier (Axon Instruments, USA). Recording electrodes with typical resistances of 4–8 MΩ were backfilled with (in mM) 108 caesium-methansulfonate, 2 MgCl$_2$, 10 HEPES, 11 EGTA, 2 ATP, pH 7.2 with CsOH. To create command potentials and acquire data, Clampex 8.2 software (Axon Instruments, USA) and a Digidata 1322A A/D converter interface (Axon Instrument, USA) were used. Currents were elicited at test potential of +20 mV (50 ms duration) from a holding potential of –80 mV. Leak and capacitance currents were subtracted on-line with a standard P/4 protocol. Evoked currents were filtered by a low-pass Bessel filter set at 1 kHz. Signals were acquired at 2.02 kHz and analyzed offline using pClamp 8.2 (Axon Instruments, USA) and Origin (OriginLab Corporation, USA) software. The effects of co-expressing the $\alpha_2\delta$ subunit of Example 1 with the rat $\alpha_{1B}+\beta_{1b}$ calcium channel subunits were tested by comparing average current density ($I_{peak}$/cell capacitance) with and without $\alpha_2\delta$.

Figure 3:
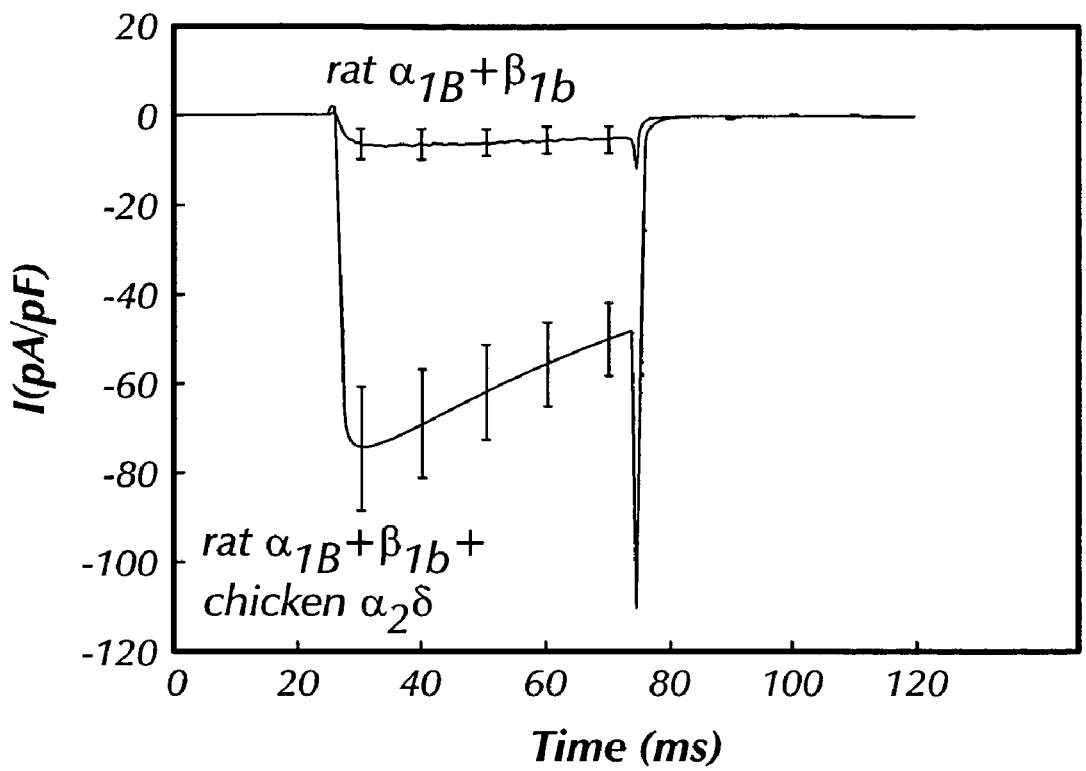
FIG. 3 shows rat $\alpha_{1B}$+$\beta_{1b}$ $Ca^{2+}$ channel current density when tested in the presence and absence of $\alpha_2\delta$-1.

Mean current density was recorded for 3 cells transfected with rat $\alpha_{1B}+\beta_{1b}$ only and 6 cells cotransfected with chicken $\alpha_2\delta$-1. The rat $\alpha_{1B}+\beta_{1b}$ current density was increased by ~10 fold from –7.1±3.5 pA/pF to –74.5±14.0 pA/pF when coexpressed with the chicken $\alpha_2\delta$ subunit. P=0.01, Student's unpaired t-test. Values are the mean±S.E.M. The results are shown in FIG. 3.

B. Transient Transfection in *Xenopus* Oocytes

Stage V and VI *Xenopus* oocytes are prepared as described by Dascal, et al., *Science* (1986) 231:1147–1150. After enzymatic dissociation with collagenase, oocyte nuclei are microinjected with the $\alpha_2\delta$ subunit cDNA expression vector construct of Example 1 (approximately 10 ng DNA per nucleus) using a Drummond nanoject apparatus, alone, or in combination with expression systems for other animal calcium channel subunits $\alpha_1$ and $\beta_{1b}$ cDNA's. After incubation from 48 to 96 hrs macroscopic currents are recorded using a standard two microelectrode voltage-clamp (Axoclamp 2A, Axon Instruments, Burlingame, Calif.) in a bathing medium containing (in mM): 40 Ba(OH)$_2$, 25 TEA-OH, 25 NaOH, 2 CsOH, 5 HEPES (pH titrated to 7.3 with methansulfonic acid). Pipettes of typical resistance ranging from 0.5 to 1.5 mΩ are filled with 2.8 M CsCl, 0.2 M CsOH, 10 mM HEPES, 10 mM BAPTA free acid. Endogenous Ca (and Ba)—activated Cl currents are suppressed by systematically injecting 10–30 nl of a solution containing 100 mM BAPTA-free acid, 10 mM HEPES (pH titrated to 7.2 with CsOH) using a third pipette connected to a pneumatic injector. Leak currents and capacitive transients are subtracted using a standard P/5 procedure.

EXAMPLE 3

Mammalian Cell Lines Stably Expressing the Chicken $\alpha_2\delta$

A. Cloning of the $\alpha_2\delta+\beta_{1b}$ Subunits into a Mammalian Expression Vector Chicken $\alpha_2\delta$ was cloned into pBud CE4 containing the rat $\beta_{1b}$ cDNA in order to make a mammalian cell line stably expressing both of these subunits. Briefly, pBK-RSV (-lac p) chicken $\alpha_2\delta$ PCR/λ clone 9 was sequentially digested with Not I and Kpn I to excise the chicken $\alpha_2\delta$ cDNA. In order to separate the $\alpha_2\delta$ fragment from the vector the DNA was digested with AvrII, then gel electrophoresed and purified using a gel extraction kit (Qiagen). The chicken $\alpha_2\delta$ fragment was subsequently ligated into pBud CE4 rat $\beta_{1b}$ at the Not I and Kpn I restriction enzyme sites. Transfection and sequencing quality cDNA were made using the QIAprep Spin Midi Kit (Qiagen). The final construct pbud CE4 rat $\beta_{1b}$+chicken $\alpha_2\delta$ was sequenced to confirm integrity of the cloning sites and cDNA orientation.

B. Transient Transfection of the Rat $\beta_{1b}$+Chicken $\alpha_2\delta$ Construct Prior to making stably expressing cell lines, the pBud CE4 rat $\beta_{1b}$+chicken $\alpha_2\delta$ construct was transiently co-transfected with the rat $\alpha_{1B}$ (N-type calcium channel) into HEK 293 cells and analyzed by patch clamp recording. Transient transfections and patch clamp recordings were done according to the protocol in Example 2, Section A.

C. HEK 293 Cells Stably Expressing Rat $\beta_{1b}$+Chicken $\alpha_2\delta$ pBud CE 4 rat $\beta_{1b}$+chicken $\alpha_2\delta$ clone 3 was linearized with Nhe I and purified by phenol/chloroform, chloroform extraction and ethanol precipitation. The digested cDNA was dissolved in sterile water for transfection. The linearized construct pBud CE4 r$\beta_{1b}$+ch$\alpha_2\delta$ was transfected into HEK 293 cells using lipofectamine (*Invitrogen Life Technologies*) in OptiMEM media and plated for selection at densities of $1.4 \times 10_5$ to $5 \times 10_5$ cells per 10 cm plate. Cells were selected in cell culture media (DMEM, 10% FBS, Non-essential amino acids) with 50 μg/ml zeocin (Invitrogen) under conditions of 37° C., 5% $CO_2$ for 14–16 days. Single colonies were picked by the pipette technique and further grown for selection, expansion and RNA production. Total RNA of the cell clones was extracted using Trizol (Invitrogen Life Technologies) following the manufactures instructions. Expression of chicken $\alpha_2\delta$ mRNA was detected by Northern blot. Rat $\beta_{1b}$ expression was determined by Western blot of whole cell lysates using an antibody to the Myc-tag epitope. Clones expressing both subunits were selected and transiently transfected with the rat $\alpha_{1B}$ (N-type calcium channel) and currents were detected by patch clamp analysis as previously described.

D. HEK 293 Cells Stably Expressing Rat $\beta_{1b}$+Chicken $\alpha_2\delta$ and Rat $\alpha_{1B}$ (N-Type Calcium Channel)

The rat CMV $\alpha_{1B}$ construct was linearized by digestion with Mfe I, purified by phenol/chloroform, chloroform extraction and ethanol precipitation. Linearized rat $\alpha_{1B}$ was transfected into HEK 293 stably expressing rat $\beta_{1b}$+chicken $\alpha_2\delta$, clone #34 and #35, as previously described above. Cells were incubated at 37 ° C., 5% $CO_2$, for 14 days in selection media containing 800 μg/ml Geneticin and 25 μg/ml Zeocin (Invitrogen Life Technologies). Single colonies were picked by the pipette technique and grown for selection and expansion, and total RNA extraction. Cell clones expressing the rat $\alpha_{1B}$ channel were detected by Northern blot and subsequently screened by patch clamp analysis for N-type currents. In addition to the patch clamp protocol described in Example 2, Section A, the current-voltage relationship and the voltage-dependence of activation and inactivation were also obtained. Current-voltage relationships were generated by applying 50 ms test pulses in 5 mV steps between −85 and 85 mV from a holding potential of −80 mV. Data collected for the current-voltage curve were then used to obtain the conductance-voltage relationship, which were fitted with a single Boltzmann equation to calculate the voltage-dependence of half-activation and the slope factor. Steady-state inactivation curves were obtained with 1 s prepulses in 5 mV steps between −100 and 20 mV from a holding potential of −100 mV followed by a 50 ms test pulse to 20 mV. The data were fitted to a single Boltzmann equation to obtain the voltage-dependence of half-inactivation and the slope factor.

EXAMPLE 4

Screening for Calcium Channel Blockers

To screen for calcium channel blockers, the whole-cell patch clamp recording technique used was as described in Example 2. Test compounds were added to the extracellular recording solution from a stock concentration of 1 mM (in DMSO) for each experiment. Compounds were then applied directly onto the HEK cells by means of a custom-made gravity-driven perfusion system, which changes the solution around the cell in less than 1 s. Differences in the mean peak current densities in the absence and presence of drugs were measured to estimate the concentration of drug required to occupy 50% of the channels ($K_d$). The $K_d$ was estimated using the equation $$K_d = a[drug]/1-a.$$

Figure 4:
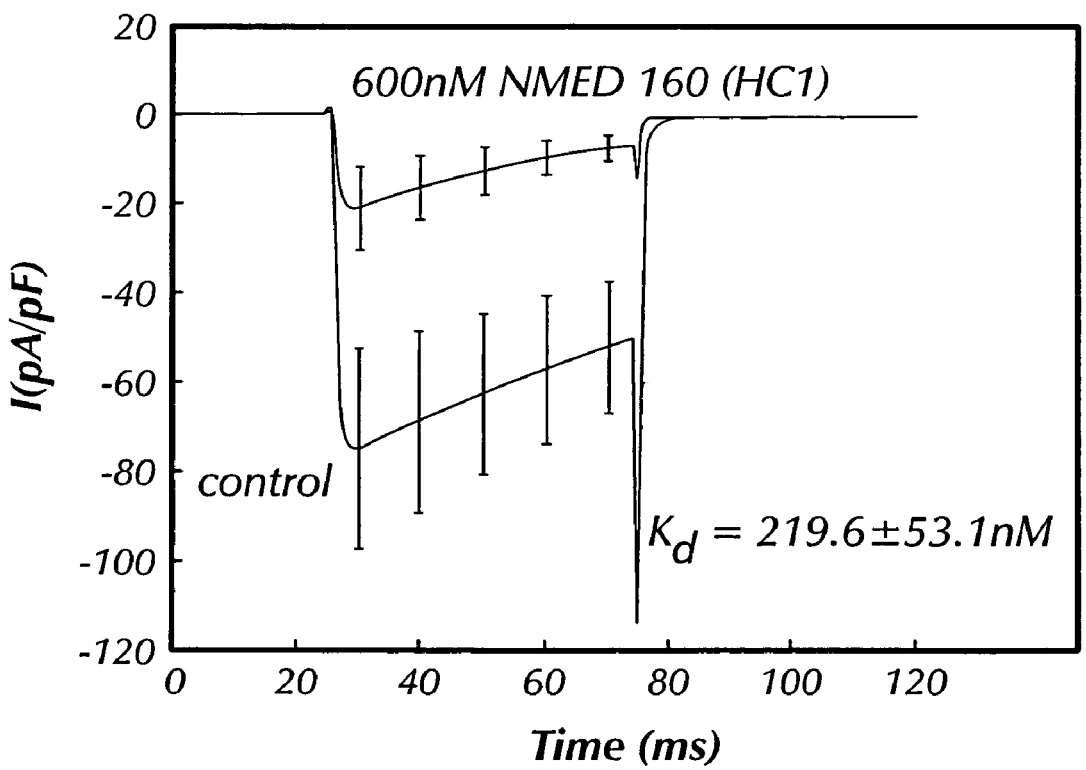
FIG. 4 shows the inhibition of rat $\alpha_{1B}$+$\beta_{1b}$+chicken $\alpha_2\delta$ $Ca^{2+}$ channel current by a $Ca^{2+}$ channel blocker designated NMED 160 (HCl).
Figure 5A:
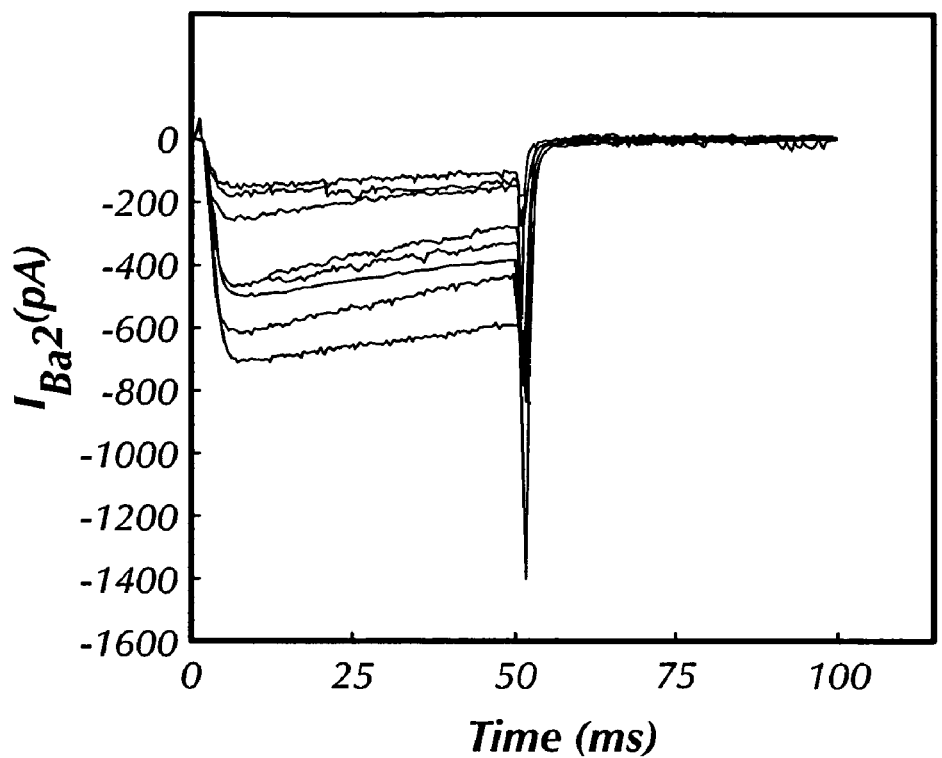
FIG. 5A–D shows the biophysical properties of stably expressed rat $\alpha_{1B}$+rat $\beta_{1b}$ chicken $\alpha_2\delta$-1 $Ca^{2+}$ channel subunits.
Figure 5B:
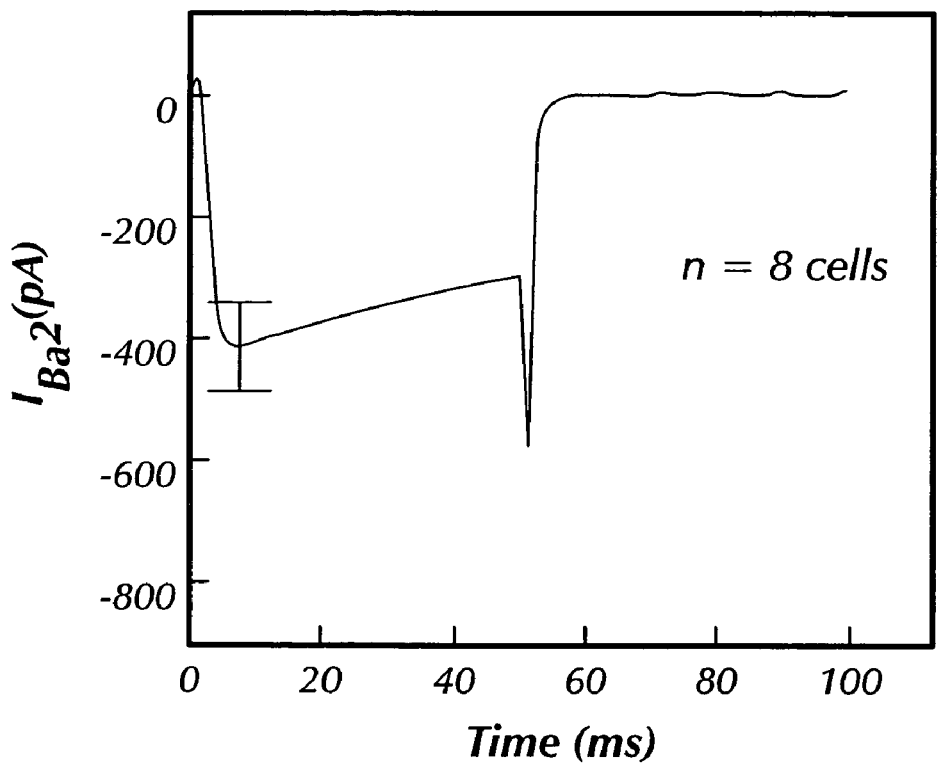
Figure 5C:
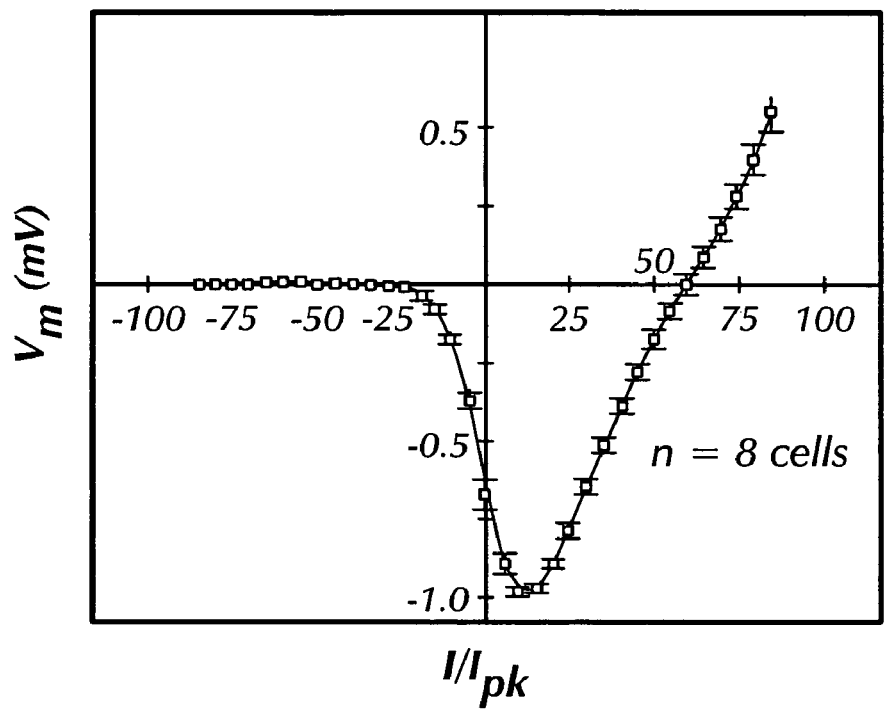
Figure 5D:
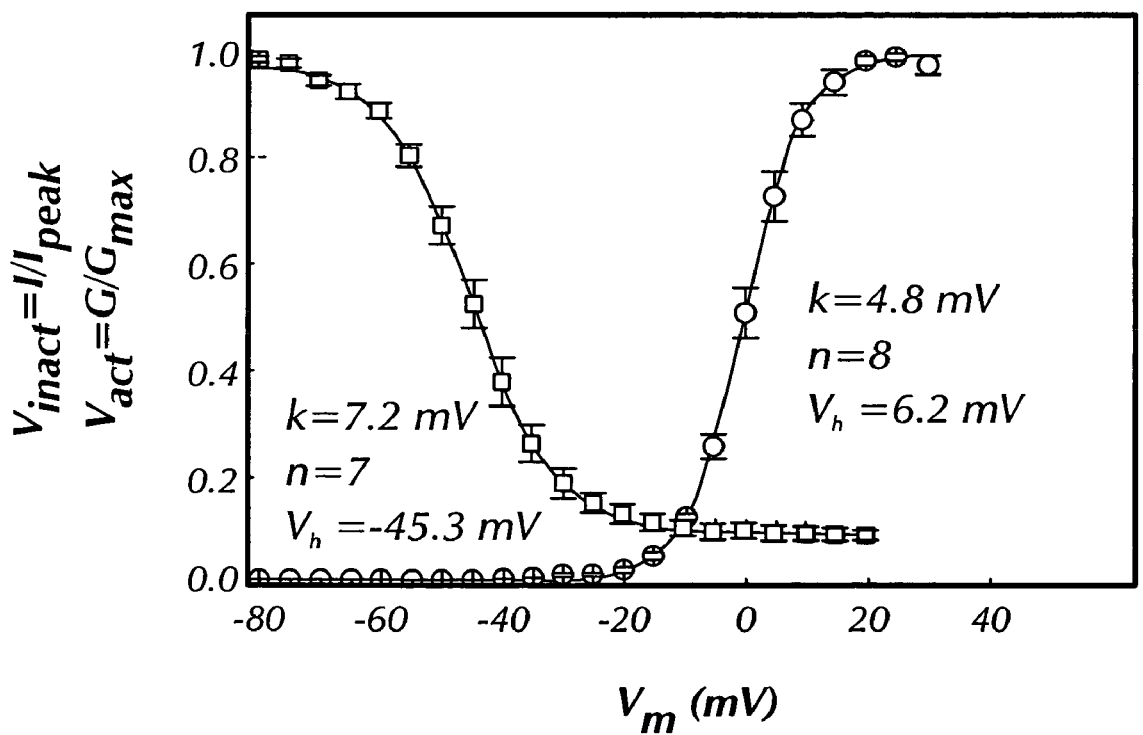

Average current density illustrating the inhibition of the rat $\alpha_{1B}$+$\beta_{1b}$+chicken $\alpha_2\delta$ $Ca^{2+}$ channel by 600 nM NMED 160 (HCl). Values are the mean±S.E.M, n=3. The results are shown in FIG. 4.

The invention claimed is:

1. An isolated or recombinant nucleic acid which comprises a nucleotide sequence that encodes a protein which functions as an $\alpha_2\delta$ calcium ion channel subunit in that when it is associated with an $\alpha_1$ subunit and optionally a $\beta$ subunit it enhances the density of current flow in the calcium ion channel thus created, and
    which protein has at least 85% sequence identity to the amino acid sequence set forth as SEQ ID NO:2.

2. The isolated or recombinant nucleic acid of claim 1, wherein said nucleotide sequence encodes a protein having at least 90% sequence identity to the amino acid sequence of SEQ ID NO:2.

3. The isolated or recombinant nucleic acid of claim 1, wherein said nucleotide sequence encodes a protein having at least 95% sequence identity to the amino acid sequence of SEQ ID NO:2.

4. The isolated or recombinant nucleic acid of claim 1, wherein said nucleotide sequence encodes a protein having the amino acid sequence of SEQ ID NO:2.

5. The isolated or recombinant nucleic acid of claim 1, wherein said nucleotide sequence has at least 85% sequence identity to SEQ ID NO:1.

6. The isolated or recombinant nucleic acid of claim 1, wherein said nucleotide sequence has at least 90% sequence identity to SEQ ID NO:1.

7. The isolated or recombinant nucleic acid of claim 1, wherein said nucleotide sequence has at least 95% sequence identity to SEQ ID NO:1.

8. The isolated or recombinant nucleic acid of claim 1, wherein said nucleotide sequence is identical to SEQ ID NO: 1.

9. A recombinant nucleic acid molecule which comprises a nucleotide sequence as set forth in claim 1, operably linked to heterologous control sequences to effect its expression.

10. The recombinant nucleic acid of claim 9, wherein said control sequences are operable in at least vertebrate cells.

11. Recombinant host cells comprising the nucleic acid molecule of claim 9.

12. Vertebrate cells comprising the nucleic acid molecule of claim 10.

13. A method to produce a recombinant protein that exhibits $\alpha_2\delta$ calcium ion channel functionality in that when it is associated with an $\alpha_1$ subunit and optionally a $\beta$ subunit it enhances the density of current flow in the calcium ion channel thus created,
which method comprises the step of culturing the recombinant host cells of claim 11 or claim 12 under conditions wherein a recombinant protein is produced by the recombinant host cells.

14. A method to produce a functional recombinant calcium ion channel displayed on a cell which method comprises
(a) providing a cell that produces an $\alpha_1$ subunit and that contains the recombinant nucleic acid molecule as set forth in claim 9; and
(b) culturing said cell under conditions wherein the nucleotide sequence of claim 9 is expressed,
thereby producing a functional recombinant calcium ion channel displayed on the cell.

15. Recombinant cells obtained in the method of claim 14.

16. A method to identify a compound that is an agonist or antagonist of calcium ion channel activity which method comprises culturing the cells of claim 15 in with presence and absence of a candidate compound,
whereby an increase in calcium ion flow in the presence as opposed to the absence of said compound identifies said candidate compound as an agonist; and
whereby a decrease in the calcium ion flow in the presence as opposed to the absence of said channel identifies said compound as an antagonist.

17. A method to detect the production of mRNA encoding an $\alpha_2\delta$ protein, which method comprises contacting mRNA to be assessed for the presence of said $\alpha_2\delta$ encoding RNA with a probe which is the complement of SEQ ID NO:1, under conditions of high stringency which are defined as 50% formamide in Church buffer at +50° C. or 65° C. in aqueous buffer, and washed at high stringency conditions comprising 0.5×SSC, 0.1% SDS to 0.1×SSC, 0.1% SDS, 65° C. to 68° C.; whereby hybridization of said probe to said RNA under said conditions demonstrates the production of $\alpha_2\delta$ encoding RNA in said sample.

18. An isolated or recombinant nucleic acid comprising (a) a nucleotide sequence that hybridizes to DNA sequence complementary to SEQ ID NO:1, wherein the conditions of high stringency comprise 50% formamide in Church buffer at +50° C. or 65° C. in aqueous buffer, and washed at high stringency conditions comprising 0.5×SSC, 0.1% SDS to 0.1×SSC, 0.1% SDS, 65° C. to 68° C., and the nucleotide sequence encodes a protein which functions as an $\alpha_2\delta$ calcium channel subunit in that when it is associated with an $\alpha_1$ subunit and optionally a $\beta$ subunit it enhances the density of current flow in the calcium ion channel thus created; or,
(b) a nucleotide sequence complementary to the full length sequence of (a).

19. The nucleic acid of claim 18, further comprising a detectable label, wherein optionally the detectable label comprises a radioactive label, a biotin, a fluorescent probe or a chemiluminescent probe.

* * * * *

SEQUENCE LISTING

```
<160> NUMBER OF SEQ ID NOS: 12

<210> SEQ ID NO 1
<211> LENGTH: 3684
<212> TYPE: DNA
<213> ORGANISM: Gallus domesticus

<400> SEQUENCE: 1
gatcttcgat caggaagatg gctgctggct ggctgctggt ctttagcctg acacttttcc        60
agtctctggt gatgaaccac tcgtcggagg gcccgttccc ttcgcccacc acgataaagt       120
catgggtaga taagatgcaa gaggacctca taacattggc acgaactgca agtggagtgg       180
aacagcttgc tgcgatatat ttgaaaaaca aagatttgta taccgtagaa gccaacaatc       240
ctcgtcagct agtggaaatt gcagccagag acattgaaaa acttctgagc aacagatcta       300
aggctttggt gcgcctcgct aaagaagcag agaagtacca agcatcacat cagtggaggg       360
atgagtttgg gaataatgat ataatctatt acaatgcaaa agatgatcag aatgatcctg       420
```

-continued

```
aaaagaatga cactgaatct ggcagccaga gaatcagacc agtatttgaa gaagatcctg    480
ttttccgacg gcaaacgtct taccaacatg cagcagttca cataccaaca gatatttatg    540
aaggctcaac aatagtgtta aatgaactca attggactgc agcactggat gatgtattca    600
agcggaacag agaagaagac cccactttat tatggcaagt ttttggtagt gcaactggcc    660
tcgctaggta ttacccagct tctccatggg tagataatag tcgaactcca aacaaaatag    720
atctatatga tgttcgcaga agaccatggt atatccaagg agctgcatct cccaaagaca    780
tgcttatttt agttgatgcg agcgggagtg tgagtggatt gacgctgaag ctgatccgca    840
catcggtcat tgagatgtta gagaccttgt ctgatgatga ctttgtgaat gtagtttcat    900
ttaataataa tgctcagaac gtcagttgct ttaatcatct tgtccaagct aatgtgagga    960
acaagaagaa gctgaaggaa gctgtggata aatctctgc taaaggaatt actgattaca   1020
aaaaaggctt tagctacgct tttgaacagc tgctcaatca cagcgtttct agagctaact   1080
gcaataagat tataatgttg tttacggatg gtggtgagga aagagcacaa gaaatattcc   1140
ataaatataa tgaagacaaa aaagtacgtg tgttcacatt ttctgttggt caacataatt   1200
atgacaaagg acctatacag tggatggcct gtgaaaataa aggttattat tatgaaattc   1260
catccattgg agccataaga ataaacaccc aggaatatct ggacgttttg ggaaggccaa   1320
tggtgttagc tggtgagaaa gccaaacagg tccaatggac aaatgtctat ctggatgctc   1380
tggagctggg ccttgtgatt acaggaactc tgcctgtctt caatctaaca aaagaacaaa   1440
atggaaaaat aaatcagctg attcttggag taatgggggt tgatgtctct ctggaagata   1500
taaaaaagct gacacctcga tttacgcttt gtccaaatgg atactacttt gcaattgatc   1560
ctaatgggta tgtgctactt catccaaatc ttcaaccaaa gaatcctaaa tcccaggagc   1620
cagtaacact ggattttcta gatgctgaac tggaaaatga tattaaagtt gagattcgga   1680
aaaaaatgat agatggagaa agtggagaaa aacatttga aactctggtc aagtcccaag   1740
atgagagata tattgataaa ggaaatcgaa catatacatg gactgctgtg aatggcactg   1800
attacagttt ggcattggtg ctaccatcat acagctttta ttatattaaa gctaaaatag   1860
aagaaccaat aactcaagcc agattggaaa tcaaaaagga ttcagaaaca ctgaagattg   1920
atcattttga tgaagctggc tatacgttta tagcaccaag agaatattgt actgatgtaa   1980
agaaatcaga aataacact gaattttgt taaattttaa tgaatttatc gatagaaata   2040
ctccaagcag tccatcatgt aatactgata tggtcattag agttctgctg gatgcaggat   2100
ttacaaatga acttgcccaa aattattgga gtaagctgta tcttgatgga gttgttgcgc   2160
aatttgttgt tacggatggt ggaattacaa gagtgttccc caaagggca ggagaagatt   2220 ggttggaaaa tgcagaaact tatgaagtca gtttctataa acggagttta gataatgaca   2280
actatatttt cacagctcca tactacaaca aaagcggtgc caatagctat gaatcaggta   2340
ttatggtaag caaggccgtg gaaataacaa ttaatggaaa acttctgaaa cctgcagttg   2400
ttggaataaa aattgatgca atgaaatgga tggaaaattt cacaacaacc acaatcaaga   2460
gcctgtgcaa cagtgaaatc tgtggctgtg aaaaaacag tatgcatgtg gactgtgtta   2520
tccttgatga tggtggattt cttctgatgt caaatcggga tgaatatacc accagattg   2580 gaagattctt tggtgaaatt gaccctggct tgatgagaaa tttaattaac atgtccctgt   2640
atgcctttaa caagtcatat gactatcaat cagtctgtga tcctgaagaa gaaccaaagc   2700
aaggagctgg acttcgttca gcttatgtgc ctacaatagc agatatttg caactaggat   2760
```

-continued

| | |
|---|---|
| ggtgggcttc agcagctgcc tggtctatct tacagcagct cttttgagc ttgactttcc | 2820 |
| cacgtttcct tgaggcagct gatatggaag atgacgattt ctctactgct ctgcctaaaa | 2880 |
| caagttgtat cactgagcaa actcagtatt tctttgaaaa tgatgataaa tcttttattg | 2940 |
| ggattgtaga ctgcatcaac tgttcaagac tttatcatgc agagaagatt tcaaacacca | 3000 |
| atctagtatt cattattagt gacagccaac tgctgtgccg ctcctgtgat ccaaagccac | 3060 |
| tgatgcaagc agagaagccg gatgaagggc caaatccttg tgaaatggtc aaacagccca | 3120 |
| gatacagaaa aggtcccgat gtctgttttg atgaagccaa acaggaagat tcggctgatt | 3180 |
| gcggtggtgc ctctggtttg agtccatcac tgtggtctat ggtaggaatt cagttggtcc | 3240 |
| tgctttggct cttatctggc agcagacact accagttatg accttgctaa aataaaacct | 3300 |
| gcataactta atcaagatcc agccaaaatg acagcctcag tttcatttta aaagggtca | 3360 |
| gctattcagg cagcagcaga acaccaatgc tcatgtctgg ttatcatgcg ttgtgagatt | 3420 |
| cataaaggca ctcaaaatgg ctgcatattg gagtgtcaat ccttaaacgt atgtgaatgc | 3480 |
| tgcatcatct ctaccaccca aacagaattc cgtacacatt tcattgggga atctaagatt | 3540 |
| ttttgtcatt catttgttgt tgtaatctca atgacttcat gtaaaagggc tcccctgacc | 3600 |
| atagtgtatg tatatgattt tcatttattt taagctttgg atttcttgaa gatttatatt | 3660 |
| cttttacatg aacatttatt tatg | 3684 |

<210> SEQ ID NO 2
<211> LENGTH: 1087
<212> TYPE: PRT
<213> ORGANISM: Gallus domesticus

<400> SEQUENCE: 2

```
Met Ala Ala Gly Trp Leu Leu Val Phe Ser Leu Thr Leu Phe Gln Ser
 1               5                  10                  15

Leu Val Met Asn His Ser Ser Glu Gly Pro Phe Pro Ser Pro Thr Thr
            20                  25                  30

Ile Lys Ser Trp Val Asp Lys Met Gln Glu Asp Leu Ile Thr Leu Ala
        35                  40                  45

Arg Thr Ala Ser Gly Val Glu Gln Leu Ala Ala Ile Tyr Leu Lys Asn
    50                  55                  60

Lys Asp Leu Tyr Thr Val Glu Ala Asn Asn Pro Arg Gln Leu Val Glu
65                  70                  75                  80

Ile Ala Ala Arg Asp Ile Glu Lys Leu Leu Ser Asn Arg Ser Lys Ala
                85                  90                  95

Leu Val Arg Leu Ala Lys Glu Ala Glu Lys Tyr Gln Ala Ser His Gln
            100                 105                 110

Trp Arg Asp Glu Phe Gly Asn Asn Asp Ile Ile Tyr Tyr Asn Ala Lys
        115                 120                 125

Asp Asp Gln Asn Asp Pro Glu Lys Asn Asp Thr Glu Ser Gly Ser Gln
    130                 135                 140

Arg Ile Arg Pro Val Phe Glu Glu Asp Pro Val Phe Arg Arg Gln Thr
145                 150                 155                 160

Ser Tyr Gln His Ala Ala Val His Ile Pro Thr Asp Ile Tyr Glu Gly
                165                 170                 175

Ser Thr Ile Val Leu Asn Glu Leu Asn Trp Thr Ala Ala Leu Asp Asp
            180                 185                 190

Val Phe Lys Arg Asn Arg Glu Glu Asp Pro Thr Leu Leu Trp Gln Val
        195                 200                 205
```

-continued

Phe Gly Ser Ala Thr Gly Leu Ala Arg Tyr Tyr Pro Ala Ser Pro Trp
210                 215                 220

Val Asp Asn Ser Arg Thr Pro Asn Lys Ile Asp Leu Tyr Asp Val Arg
225                 230                 235                 240

Arg Arg Pro Trp Tyr Ile Gln Gly Ala Ala Ser Pro Lys Asp Met Leu
            245                 250                 255

Ile Leu Val Asp Ala Ser Gly Ser Val Ser Gly Leu Thr Leu Lys Leu
                260                 265                 270

Ile Arg Thr Ser Val Ile Glu Met Leu Glu Thr Leu Ser Asp Asp Asp
        275                 280                 285

Phe Val Asn Val Val Ser Phe Asn Asn Asn Ala Gln Asn Val Ser Cys
290                 295                 300

Phe Asn His Leu Val Gln Ala Asn Val Arg Asn Lys Lys Leu Lys
305                 310                 315                 320

Glu Ala Val Asp Lys Ile Ser Ala Lys Gly Ile Thr Asp Tyr Lys Lys
                325                 330                 335

Gly Phe Ser Tyr Ala Phe Glu Gln Leu Leu Asn His Ser Val Ser Arg
                340                 345                 350

Ala Asn Cys Asn Lys Ile Ile Met Leu Phe Thr Asp Gly Gly Glu Glu
            355                 360                 365

Arg Ala Gln Glu Ile Phe His Lys Tyr Asn Glu Asp Lys Lys Val Arg
370                 375                 380

Val Phe Thr Phe Ser Val Gly Gln His Asn Tyr Asp Lys Gly Pro Ile
385                 390                 395                 400

Gln Trp Met Ala Cys Glu Asn Lys Gly Tyr Tyr Glu Ile Pro Ser
            405                 410                 415

Ile Gly Ala Ile Arg Ile Asn Thr Gln Glu Tyr Leu Asp Val Leu Gly
                420                 425                 430

Arg Pro Met Val Leu Ala Gly Glu Lys Ala Lys Gln Val Gln Trp Thr
        435                 440                 445

Asn Val Tyr Leu Asp Ala Leu Glu Leu Gly Leu Val Ile Thr Gly Thr
450                 455                 460

Leu Pro Val Phe Asn Leu Thr Lys Glu Gln Asn Gly Lys Ile Asn Gln
465                 470                 475                 480

Leu Ile Leu Gly Val Met Gly Val Asp Val Ser Leu Glu Asp Ile Lys
                485                 490                 495

Lys Leu Thr Pro Arg Phe Thr Leu Cys Pro Asn Gly Tyr Tyr Phe Ala
            500                 505                 510

Ile Asp Pro Asn Gly Tyr Val Leu Leu His Pro Asn Leu Gln Pro Lys
    515                 520                 525

Asn Pro Lys Ser Gln Glu Pro Val Thr Leu Asp Phe Leu Asp Ala Glu
    530                 535                 540

Leu Glu Asn Asp Ile Lys Val Glu Ile Arg Lys Lys Met Ile Asp Gly
545                 550                 555                 560

Glu Ser Gly Glu Lys Thr Phe Glu Thr Leu Val Lys Ser Gln Asp Glu
            565                 570                 575

Arg Tyr Ile Asp Lys Gly Asn Arg Thr Tyr Thr Trp Thr Ala Val Asn
            580                 585                 590

Gly Thr Asp Tyr Ser Leu Ala Leu Val Leu Pro Ser Tyr Ser Phe Tyr
        595                 600                 605

Tyr Ile Lys Ala Lys Ile Glu Glu Pro Ile Thr Gln Ala Arg Leu Glu
610                 615                 620

Ile Lys Lys Asp Ser Glu Thr Leu Lys Ile Asp His Phe Asp Glu Ala

-continued

```
            625                 630                 635                 640
Gly Tyr Thr Phe Ile Ala Pro Arg Glu Tyr Cys Thr Asp Val Lys Lys
                        645                 650                 655
Ser Glu Asn Asn Thr Glu Phe Leu Leu Asn Phe Asn Glu Phe Ile Asp
                660                 665                 670
Arg Asn Thr Pro Ser Ser Pro Ser Cys Asn Thr Asp Met Val Ile Arg
            675                 680                 685
Val Leu Leu Asp Ala Gly Phe Thr Asn Glu Leu Ala Gln Asn Tyr Trp
        690                 695                 700
Ser Lys Leu Tyr Leu Asp Gly Val Val Ala Gln Phe Val Val Thr Asp
705                 710                 715                 720
Gly Gly Ile Thr Arg Val Phe Pro Lys Arg Ala Gly Glu Asp Trp Leu
                    725                 730                 735
Glu Asn Ala Glu Thr Tyr Glu Val Ser Phe Tyr Lys Arg Ser Leu Asp
                740                 745                 750
Asn Asp Asn Tyr Ile Phe Thr Ala Pro Tyr Tyr Asn Lys Ser Gly Ala
            755                 760                 765
Asn Ser Tyr Glu Ser Gly Ile Met Val Ser Lys Ala Val Glu Ile Thr
        770                 775                 780
Ile Asn Gly Lys Leu Leu Lys Pro Ala Val Val Gly Ile Lys Ile Asp
785                 790                 795                 800
Ala Met Lys Trp Met Glu Asn Phe Thr Thr Thr Ile Lys Ser Leu
                    805                 810                 815
Cys Asn Ser Glu Ile Cys Gly Cys Glu Lys Asn Ser Met His Val Asp
                820                 825                 830
Cys Val Ile Leu Asp Asp Gly Gly Phe Leu Leu Met Ser Asn Arg Asp
            835                 840                 845
Glu Tyr Thr His Gln Ile Gly Arg Phe Phe Gly Glu Ile Asp Pro Gly
        850                 855                 860
Leu Met Arg Asn Leu Ile Asn Met Ser Leu Tyr Ala Phe Asn Lys Ser
865                 870                 875                 880
Tyr Asp Tyr Gln Ser Val Cys Asp Pro Glu Glu Glu Pro Lys Gln Gly
                    885                 890                 895
Ala Gly Leu Arg Ser Ala Tyr Val Pro Thr Ile Ala Asp Ile Leu Gln
                900                 905                 910
Leu Gly Trp Trp Ala Ser Ala Ala Trp Ser Ile Leu Gln Gln Leu
            915                 920                 925
Phe Leu Ser Leu Thr Phe Pro Arg Phe Leu Glu Ala Ala Asp Met Glu
        930                 935                 940
Asp Asp Asp Phe Ser Thr Ala Leu Pro Lys Thr Ser Cys Ile Thr Glu
945                 950                 955                 960
Gln Thr Gln Tyr Phe Phe Glu Asn Asp Asp Lys Ser Phe Ile Gly Ile
                    965                 970                 975
Val Asp Cys Ile Asn Cys Ser Arg Leu Tyr His Ala Glu Lys Ile Ser
                980                 985                 990
Asn Thr Asn Leu Val Phe Ile Ile Ser Asp Ser Gln Leu Leu Cys Arg
            995                 1000                1005
Ser Cys Asp Pro Lys Pro Leu Met Gln Ala Glu Lys Pro Asp Glu Gly
        1010                1015                1020
Pro Asn Pro Cys Glu Met Val Lys Gln Pro Arg Tyr Arg Lys Gly Pro
1025                1030                1035                1040
Asp Val Cys Phe Asp Glu Ala Lys Gln Glu Asp Ser Ala Asp Cys Gly
                    1045                1050                1055
```

Gly Ala Ser Gly Leu Ser Pro Ser Leu Trp Ser Met Val Gly Ile Gln
            1060                1065                1070

Leu Val Leu Leu Trp Leu Leu Ser Gly Ser Arg His Tyr Gln Leu
        1075                1080                1085

<210> SEQ ID NO 3
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 13, 17
<223> OTHER INFORMATION: n = inosine

<400> SEQUENCE: 3
gcctgctggc ctngacnctg acac                                    24

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ccgtcactat caagtcatgg gtg                                     23

<210> SEQ ID NO 5
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 8
<223> OTHER INFORMATION: n = inosine

<400> SEQUENCE: 5
ggtcayanya gtagtgtctg ctgccag                                 27

<210> SEQ ID NO 6
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 9, 15
<223> OTHER INFORMATION: n = inosine

<400> SEQUENCE: 6
acaccaccnc agtcngtata atcctc                                  26

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
agaggaccta ttcagtggat ggc                                     23

-continued

```
<210> SEQ ID NO 8
<211> LENGTH: 25
<212> TYPE: DNA
<213> ORGANISM: Artificial Sequence
<220> FEATURE:
<223> OTHER INFORMATION: Primer

<400> SEQUENCE: 8
caagccatcc actgaatagg tcctc                                          25

<210> SEQ ID NO 9
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 7
<223> OTHER INFORMATION: n = inosine

<400> SEQUENCE: 9
tcytcgntcg cgaagatggc tgc                                            23

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
ggatgaagta gcacataccc attagg                                         26

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
gtagtatcca tttggacaaa gcgt                                           24

<210> SEQ ID NO 12
<211> LENGTH: 25
<212> TYPE: DNA
<213> ORGANISM: Artificial Sequence
<220> FEATURE:
<223> OTHER INFORMATION: Primer

<400> SEQUENCE: 12
aatactggtc tgattctctg gctgc                                          25
```